(12) United States Patent
Ansorge et al.

(10) Patent No.: US 12,233,285 B2
(45) Date of Patent: Feb. 25, 2025

(54) SYSTEMS, METHODS, AND DEVICES FOR RADIATION BEAM ASYMMETRY MEASUREMENTS USING ELECTRONIC PORTAL IMAGING DEVICES

(71) Applicant: Siemens Healthineers International AG, Steinhausen (CH)

(72) Inventors: Reto Ansorge, Zurich (CH); Mathias Lehmann, Zurich (CH); Stefan J. Thieme-Marti, Windisch (CH)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

(21) Appl. No.: 18/197,978

(22) Filed: May 16, 2023

(65) Prior Publication Data

US 2024/0017095 A1   Jan. 18, 2024

Related U.S. Application Data

(63) Continuation of application No. 17/523,544, filed on Nov. 10, 2021, now Pat. No. 11,691,031, which is a continuation of application No. 16/846,935, filed on Apr. 13, 2020, now Pat. No. 11,207,546, which is a continuation of application No. 15/449,586, filed on Mar. 3, 2017, now Pat. No. 10,682,528.

(51) Int. Cl.
*A61N 5/10* (2006.01)
*G01T 1/29* (2006.01)

(52) U.S. Cl.
CPC .......... *A61N 5/1075* (2013.01); *G01T 1/2914* (2013.01); *A61N 5/1045* (2013.01); *A61N 2005/1076* (2013.01); *A61N 5/1081* (2013.01); *A61N 2005/1089* (2013.01); *A61N 2005/1091* (2013.01)

(58) Field of Classification Search
None
See application file for complete search history.

(56) References Cited

U.S. PATENT DOCUMENTS

| | | |
|---|---|---|
| 4,058,730 A | 11/1977 | Meyer et al. |
| 4,729,099 A | 3/1988 | Iverson et al. |
| (Continued) | | |

FOREIGN PATENT DOCUMENTS

| | | |
|---|---|---|
| EP | 3 202 458 A2 | 8/2017 |
| JP | H-10300899 A | 11/1998 |
| JP | 3748423 B2 | 2/2006 |

OTHER PUBLICATIONS

Arnfield et al., "A method for determining multileaf collimator transmission and scatter for dynamic intensity modulated radiotherapy," Medical Physics, vol. 27, No. 10, Oct. 2000, pp. 2231-2241.

(Continued)

*Primary Examiner* — Thomas R Artman
(74) *Attorney, Agent, or Firm* — Potomac Law Group, PLLC

(57) ABSTRACT

Systems and methods for determining beam asymmetry in a radiation treatment system using electronic portal imaging devices (EPIDs) without implementation of elaborate and complex EPID calibration procedures. The beam asymmetry is determined based on radiation scattered from different points in the radiation beam and measured with the same region of interest ROI of the EPID.

12 Claims, 20 Drawing Sheets

Asymmetric Beam

(56) References Cited

U.S. PATENT DOCUMENTS

| | | | |
|---|---|---|---|
| 5,612,988 | A | 3/1997 | Martens |
| 6,097,787 | A | 8/2000 | Siochi |
| 6,108,400 | A | 8/2000 | Siochi |
| 6,167,114 | A | 12/2000 | Siochi |
| 6,353,655 | B1 | 3/2002 | Siochi |
| 6,405,072 | B1 | 6/2002 | Cosman |
| 6,636,622 | B2 | 10/2003 | Mackie et al. |
| 6,757,355 | B1 | 6/2004 | Siochi |
| 7,486,983 | B2 | 2/2009 | Ghelmansarai et al. |
| 7,531,810 | B2 | 5/2009 | Wu |
| 7,656,518 | B2 | 2/2010 | Den Boef et al. |
| 7,924,431 | B2 | 4/2011 | Giglio et al. |
| 7,957,507 | B2 | 6/2011 | Cadman |
| 8,340,460 | B2 | 12/2012 | Deutschmann |
| 8,436,316 | B2 | 5/2013 | Taleyarkhan |
| 8,921,766 | B2 | 12/2014 | Schiefer |
| 8,983,165 | B2 * | 3/2015 | Sun ...................... A61B 6/5205 600/407 |
| 9,201,151 | B2 | 12/2015 | Taleyarkhan |
| 9,786,044 | B2 * | 10/2017 | Fuchs ...................... G06T 7/11 |
| 9,844,358 | B2 | 12/2017 | Wiggers et al. |
| 10,022,564 | B2 | 7/2018 | Thieme et al. |
| 10,039,519 | B2 * | 8/2018 | Brown .................... A61B 6/584 |
| 10,327,717 | B2 * | 6/2019 | Melman ............... A61B 6/4225 |
| 10,682,528 | B2 | 6/2020 | Ansorge et al. |
| 11,058,393 | B2 | 7/2021 | Wiggers |
| 11,207,546 | B2 | 12/2021 | Ansorge |
| 11,648,421 | B2 * | 5/2023 | Constantin ........... A61N 5/1075 250/492.3 |
| 11,691,031 | B2 * | 7/2023 | Ansorge ............... A61N 5/1075 378/65 |
| 11,724,127 | B2 * | 8/2023 | Constantin ........... A61N 5/1075 250/492.3 |
| 11,992,359 | B2 * | 5/2024 | Wiggers ............... A61N 5/1075 |
| 2002/0080912 | A1 * | 6/2002 | Mackie ................ A61N 5/1048 398/182 |
| 2004/0158145 | A1 * | 8/2004 | Ghelmansarai ....... A61N 5/1048 378/65 |
| 2006/0193441 | A1 * | 8/2006 | Cadman ............... A61N 5/1042 378/153 |
| 2007/0029508 | A1 * | 2/2007 | Wu ....................... A61N 5/1048 250/492.23 |
| 2008/0031414 | A1 | 2/2008 | Coppens |
| 2008/0239318 | A1 * | 10/2008 | Den Boef .......... G01N 21/4785 356/615 |
| 2009/0129659 | A1 * | 5/2009 | Deutschmann ....... A61N 5/1048 250/252.1 |
| 2010/0141945 | A1 * | 6/2010 | Giglio ................ G01N 15/1459 356/337 |
| 2011/0174990 | A1 | 7/2011 | Taleyarkhan |
| 2012/0014618 | A1 * | 1/2012 | Sun ....................... A61B 6/4266 382/286 |
| 2012/0305793 | A1 | 12/2012 | Schiefer |
| 2014/0008537 | A1 | 1/2014 | Taleyarkhan |
| 2015/0352376 | A1 | 12/2015 | Wiggers et al. |
| 2016/0114190 | A1 * | 4/2016 | Brown .................... A61B 6/584 378/205 |
| 2016/0180517 | A1 | 6/2016 | Fuchs et al. |
| 2016/0192892 | A1 | 7/2016 | Guez et al. |
| 2017/0199288 | A1 | 7/2017 | Taleyarkhan |
| 2017/0225015 | A1 | 8/2017 | Thieme et al. |
| 2018/0028143 | A1 | 2/2018 | Wiggers et al. |
| 2018/0250531 | A1 | 9/2018 | Ansorge et al. |
| 2018/0272155 | A1 | 9/2018 | Thieme et al. |
| 2020/0238105 | A1 | 7/2020 | Ansorge et al. |
| 2022/0062659 | A1 | 3/2022 | Ansorge |
| 2022/0314028 | A1 * | 10/2022 | Constantin ........... A61N 5/1043 |
| 2022/0314029 | A1 * | 10/2022 | Constantin ........... A61N 5/1048 |
| 2024/0017095 | A1 * | 1/2024 | Ansorge ................ G01T 1/2914 |

OTHER PUBLICATIONS

Liu et al., "Assessment of flatness and symmetry of megavoltage x-ray beam with an electronic portal imaging device (EPID)," Australian Physical and Engineering Sciences in Medicine, vol. 25, No. 2, 2002, pp. 58-67.

Chegeni et al., "Equivalent field calculation to irregular symmetric and asymmetric photon fields," World Academy of Science, Engineering and Technology International Journal of Mathematical, Computational, Physical, Electrical and Computer Engineering, vol. 7, No. 9, 2013.

His et al., "Limited accuracy of dose calculation for large fields at deep depths using the BrainSCAN v5.21 treatment-planning system," Journal of Applied Clinical Medical Physics, vol. 6, No. 2, 2005, pp. 12-18.

Gibbons, "Monitor unit calculations for external photon and electron beams," AAPM Annual Meeting Refresher Course, Salt Lake City, Utah, Jul. 25, 2001.

Yousif et al., "Performance evaluation of the Siemens electronic portal imaging device for IMTR plan verification," International Journal of Medical Physics, Clinical Engineering and Radiation Oncology, 2015, 4, pp. 215-223.

Ricz et al., "Experimental observation of left-right asymmetry in outer s-shell photoionization," IOP Publishing and Deutsche Physikalische Gesellschaft, New Journal of Physics, vol. 9, Aug. 2007.

Jeffcoat et al., "Design of gamma ray collimators for nondestructive assay," WSRC-MS-2001-00475. http://sti.srs.gov/fulltext/ms2001475/ms2001475.html.

Papatheodorou et al., "The "equivalent wedge" implementation of the Varian Enhanced Dynamic Wedge (EDW) into a treatment planning system," Physics in Medicine and Biology, vol. 44, No. 2, 1999, pp. 509-524.

Richmond et al., "Empirical determination of collimator scatter data for use in Radcalc commercial monitor unit calculation software: Implication for prostate volumetric modulated-arc therapy calculations," Medical Dosimetry, vol. 41, 2016, pp. 53-58.

International Preliminary Report and Written Opinion issued Sep. 12, 2019, in the International Application No. PCT/EP2018/055069.

International Preliminary Report and Written Opinion issued Jun. 5, 2018, in the International Application No. PCT/EP2018/055069.

* cited by examiner

Symmetric Beam

Asymmetric Beam

SYSTEMS, METHODS, AND DEVICES FOR RADIATION BEAM ASYMMETRY MEASUREMENTS USING ELECTRONIC PORTAL IMAGING DEVICES

FIELD

The present disclosure relates generally to radiation therapy, and more specifically to systems and methods for using electronic portal imaging devices (EPIDs) as radiation beam asymmetry measuring devices without the need for implementing elaborate EPID calibration processes.

BACKGROUND

In radiosurgery or radiotherapy (collectively referred to as radiation therapy) very intense and precisely collimated doses of radiation are delivered to a target region (volume of tumorous tissue) in the body of a patient in order to treat or destroy tumors or other lesions such as blood clots, cysts, aneurysms or inflammatory masses, for example. Patients undergoing radiation therapy are typically placed on the treatment platform of a radiation treatment gantry. The radiation beam irradiates a region of interest in the patient, such as a diseased tissue including a tumor or cancerous growth site. When delivering the radiation, a plurality of radiation beams may be directed to the target area of interest from several positions outside the body.

The goal of radiation therapy is to accurately deliver a prescribed radiation dose to the tumor/lesion and spare the surrounding healthy tissue. The geometric accuracy of patient positioning relative to the treatment beam, as well as the location and amount of dose delivered to the patient is therefore important. There are a number of factors that could affect geometric and dose delivery accuracy, including but not limited to, radiation beam symmetry. A radiation beam which is not symmetric may introduce errors in the radiation beam delivered onto the patient.

Beam symmetry depends on the accurate alignment and placement of various mechanical elements/pieces of the radiation therapy system. Therefore, the mechanical elements need to be checked and tuned prior to the radiation treatment device being installed and/or used in the radiation treatment facility. Because the mechanical elements affecting beam symmetry tend to move, the beam symmetry needs also to be regularly checked and, if a shift or movement is observed from the mechanical elements' nominal preset values, the mechanical elements need to be adjusted and retuned during installment, and verified during regular preventive maintenance inspection. Also, the radiation dose amount and dose placement need to be sufficiently controlled for accurate patient treatment. Therefore, the radiation therapy machine itself needs to be properly tuned at the outset (on the production floor), and then continuously monitored through periodic checks, such as, during initial installation or during routine usage of the machine by the customer, to ensure that the system is operating within appropriate and expected parameters and standards, such as, but not limited to, standards prescribed by a nationally recognized regulatory groups, such as, the American College of Radiology (ACR), the American Association of Physicists in Medicine (AAPM), or the Society for Imaging Informatics in Medicine (SIIM), for example.

Electronic portal imaging devices (EPIDs) have been previously used for evaluating beam symmetry and for verification of treatment beams. Generally, these EPIDs are used as relative dose or absolute dose measuring devices, whereby images obtained using an EPID are compared with previously obtained images, and the discrepancies between the images are associated with the parameters of the system. However, in order to make such a comparison, the images must be corrected for non-linear behavior of the electronics, inhomogeneous pixel sensitivities, scattering in the detector, and the EPID panel's complex energy response. These correction methods are complex. For example, EPIDs used as relative dose measurement devices require an external reference measurement of some sort, and the corresponding calibration schemes are often tedious. EPIDs used as absolute dose measuring devices on the other hand require complex and time-consuming calibration techniques to correct for non-linearity of the EPID response. These calibration techniques also require accurate motion control of the EPID.

There is thus a need for methods, systems, and devices by which EPIDs can be used as measurement devices for beam symmetry and beam alignment without having to implement elaborate calibration procedures. Since many of the modern radiation treatment devices, such as medical LINACS, are equipped with electronic portal imaging devices (EPIDs), there is a need for a process that enables using the EPIDs as beam alignment measuring devices without extensive calibration protocols in place, in order to perform automatic calibration, tuning, and verification of the radiation treatment systems and devices. Since currently available radiation therapy machine tuning, calibration, and verification protocols are slow, inaccurate, require external hardware, and/or rely on subjective human decisions, this would reduce overall costs, processing, and analysis time, as well as remove operator dependency.

SUMMARY

An object of the present disclosure is to provide a system and method for using an electronic portal imaging device (EPID) as a radiation beam symmetry determining device and beam alignment device without the need for extensive EPID calibration.

In exemplary embodiments, beam symmetry is determined by generating scattered radiation at a plurality of points in a radiation beam, measuring the radiation scattered from the plurality of points using the same region of interest ROI of the imaging device, and determining a beam asymmetry value based on the measured scattered radiation.

In an embodiment, the ROI is a circular ROI that has a center located at the same position as the projection of the collimator rotation axis on the imaging plane of the imaging device. In other embodiments, the ROI is not circularly symmetric around the projection of the collimator rotation axis on the imaging device. In another exemplary embodiment, the radiation delivery system includes a collimator, and the generating of the scattered radiation at the plurality of points in the radiation beam includes generating an off-axis field using the collimator, rotating the collimator around a collimator rotation axis from a first collimator location to a plurality of different subsequent collimator locations, and illuminating the collimator with the radiation beam at the first and subsequent collimator locations. The beam asymmetry value can be calculated using:

$A_{ij}=(p_i-p_j)/(p_i+p_j)$, where $A_{ij}$ is the asymmetry value, $p_i$ is an amplitude of the scattered radiation measured at the first collimator location, and $p_j$ is an amplitude of the scattered radiation measured at a second subsequent collimator location.

In another exemplary embodiment, the radiation beam tilt relative to the collimator axis of rotation can also be determined using the calculated asymmetry value. The radiation beam can be further aligned automatically and/or manually based on the determined radiation beam tilt.

In other exemplary embodiments, a method of determining radiation beam asymmetry is disclosed, comprising: moving a scatter probe from a first location to a second, symmetric location in a radiation field, irradiating the scatter probe at the first and second locations with radiation, measuring radiation scattered by the scatter probe at the first location and radiation scattered by the scatter probe at the second location using an imaging device, and calculating a beam asymmetry value based on the measured scattered radiations. The scattered radiation can be created by a small off-axis field which can be generated using a collimator, and the moving of the scatter probe can be done by moving the collimator around a collimator rotation axis from a first to a second collimator location.

In embodiments, the measuring of the scattered radiation at the first location includes detecting in a detection plane of the imaging device a plurality of first intensity values from pixels located in a region of interest ROI of the imaging device and determining a first amplitude of the scattered radiation (p) based on the plurality of first intensity values, and the measuring of the scattered radiation at the second location includes detecting a plurality of second intensity values from the pixels located in the same region of interest ROI of the imaging device and determining a second amplitude of the scattered radiation ($p_j$) based on the second pixel intensity values. In embodiments, the region of interest ROI is a region that is circularly symmetric around a projection of the collimator rotation axis on the plane of the imaging device.

In embodiments, a radiation treatment system for implementing disclosed beam symmetry determination methods based on scattering radiation measurements from different scattering locations in the radiation beam is also disclosed, the system exemplarily comprising: a radiation source to emit a radiation beam, a collimator configured to shape the radiation beam, an imaging device configured to detect the radiation beam, and a processing device configured to execute processor-executable process steps for determining radiation beam characteristics without implementing an imaging device response calibration protocol, the process steps comprising:

generating scattered radiation from a plurality of points in the radiation beam;
measuring the scattered radiation from the plurality of points using the imaging device;
determining one or more characteristics of the radiation beam from the measured scattered radiation; and
calibrating the radiation treatment system based on the determined one or more radiation beam characteristics.

In embodiments, the measuring of the scattered radiation includes measuring the scattered radiation using pixels of the imaging device positioned in the same region of interest ROI of the imaging device for each of the plurality of points in the radiation beam. The region of interest ROI can be a region that is circularly symmetric around a projection of the collimator rotation axis on the plane of the imaging device.

The present disclosure also provides using an EPID as a measuring device for detecting beam asymmetry in a radiation treatment device, calculating an asymmetry value from the detected asymmetry, and using the asymmetry value to modify the performance of the radiation therapy system to achieve the desired tuning and calibration of the system.

Another object of the present invention is to provide methods for automatic calibration, tuning, and verification of radiation treatment devices and systems to eliminate beam asymmetry using an uncalibrated EPID.

Another object of the present invention is to provide specific procedures and algorithms for the automatic tuning, calibration, and verification protocols using an EPID as a beam asymmetry measuring and beam alignment device without having to implement complex calibration procedures.

The present disclosure also provides radiation treatment systems, comprising: a radiation source configured to emit a radiation beam, an imaging device configured to acquire one or more images, and a processing device configured to execute processor-executable process steps for determining radiation beam characteristics without implementing an imaging device response calibration protocol.

The present disclosure also provides for systems and methods for calibrating the radiation treatment system based on the determined one or more radiation beam characteristics. The calibrating can include calibrating control elements of the radiation treatment system, the control elements controlling the characteristics of the radiation beam. The control elements can include one or more of beam collimator devices, beam angle steering coils, beam positon steering coils, shunt current sources, beam flattening filters, beam scattering filters, dosimeters, gantry positioning devices, light sources, beam sources, and gun-cathode heating controls.

The present disclosure also provides systems, devices, and methods for fast and less error prone tuning, calibration, and verification of radiation therapy systems based on scattering measurements obtained using electronic portal imaging devices, without the implementation of an EPID response calibration procedure.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features.

DETAILED DESCRIPTION

Figure 1:
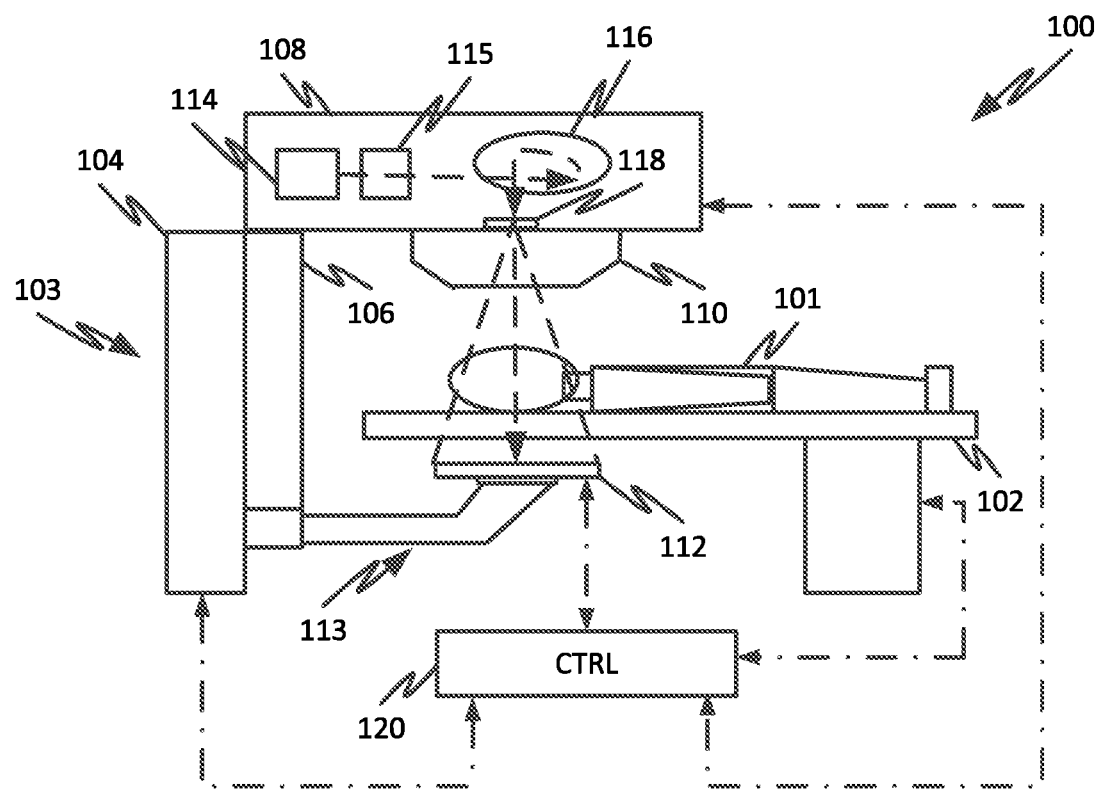
FIG. 1 illustrates a radiation treatment system according to one or more embodiments of the disclosed subject matter.

An exemplary radiation therapy treatment system which uses an EPID as a beam symmetry measuring device is illustrated in FIG. 1. The treatment system 100 is configured to deliver radiation treatment to a patient 101. The treatment system 100 can be configured for dual-mode stereotactic or radiation therapy application, namely, the system 100 can be configured to provide photon-based or electron-beam based radiation treatment to a patient 101 positioned on a treatment couch 102. The gantry 106 can be a ring gantry (i.e., it extends through a full 360° arc to create a complete ring or circle), but other types of mounting arrangements may also be employed. For example, a static beam, or a C-type, partial ring gantry, or robotic arm can be used. Any other framework capable of positioning the treatment beam source at various rotational and/or axial positions relative to the patient 101 may also be used. The system 100 also includes a treatment couch 102 which can be positioned adjacent to the gantry 106 to place the patient 101 and the target volume within the range of operation of the treatment beam during radiation treatment. The treatment couch 102 may be connected to the rotatable gantry 106 via a communications network and is capable of translating in multiple planes to reposition the patient 101 and the target volume. The treatment couch 102 can have three or more degrees of freedom.

The radiation therapy system 100 includes a radiation treatment device 103, such as, but not limited to, a dual-mode (photon and electron-beam) medical LINAC device configured for stereotactic or radiation therapy application. The radiotherapy device 103 includes a base or support structure 104 supporting the gantry 106. The gantry 106 is supporting an electron beam accelerator module 108 which can include an electron gun 114 for generating electron beams and an accelerator waveguide 115 for accelerating the electron beams from the electron gun 114 toward an X-ray target 118 (when the radiation treatment device 103 operates in a photon mode) or toward an electron beam exit window (not shown), when the radiation treatment device 103 operates in an electron-beam mode. The electron beam exit window allows the electron beam to exit the electron beam accelerator module 108 and enter a LINAC treatment head 110. The accelerating waveguide 115 can be mounted parallel to the gantry rotation axis, and thus the accelerated electron beam must be bent for it to strike the X-ray target 118 (when device 103 operates in the photon mode) or the exit window (when device 103 operates in an electron-beam mode). The accelerating waveguide 115 can also be mounted parallel to the collimator rotation axis. An electron beam transport system 116 can include bending magnets, steering coils, trim coils, and a gun cathode heating circuit can be used for bending and steering the accelerated electron beams toward the X-ray target 118 or the exit window. In alternative embodiments, the electron beam transport system 116 does not include bending magnets. The electron beam transport system 116 can bend an electron beam at 90 degrees, 270 degrees (achromatic bending) and at 112.5 degrees (slalom bending) by adjusting the shunt current applied to the bend magnet from a current source (not shown). When the electron pencil beam hits the X-ray target 118, it generates the clinical photon beams (X-rays, i.e., treatment beam). The location at which the X-rays are generated is referred to as the radiation beam spot or radiation source.

In operation, electrons originating in the electron gun 114 are accelerated in the accelerating waveguide 115 to the desired kinetic energy and then brought, in the form of a pencil electron beam, through the beam accelerator module 108 into the LINAC treatment head 110, where the clinical photons, such as X-rays, (when the device 103 operates in the photon mode) or the electron beams (when device 103 operates in the electron-beam mode) are produced. The LINAC treatment head 110 contains several components that influence the production, shaping, localizing, and monitoring of the clinical photon beams, as shown in detail in FIG. 3, or the clinical electron beams, as shown in detail in FIG. 4.

The radiation treatment device 103 also includes a holding structure 113, which could be a retractable robotic, servo controlled arm, holding an imager 112 for acquiring digital images. The imager 112 is an electronic portal imaging device (EPID). The holding structure 113 is used to position the EPID 112 and allows for the movement of the EPID 112 vertically (along the Z-axis), laterally (along the X-axis), and longitudinally (along the Y-axis). The EPID 112 can be mounted onto the rotating gantry 106 in opposition to the radiation source, such that the clinical radiation beam, namely the photon or the electron beam, from the LINAC head 110 is received by the EPID 112. The EPID 112 can have a detector surface corresponding to the cross-sectional area of the clinical radiation beam.

In operation, the EPID 112 produces electronic signals providing measurements of the radiation received at the detector surface at regularly spaced positions over the detector surface. The signals from the EPID 112 are transmitted to a computer processor of the controller 120 where it is converted into a matrix of digital values, the values indicating the dose of radiation at each point of the imager surface. A projection image derived from the matrix of digital values can be displayed on a display of the controller 120.

The controller 120 manages images and related information, such as transforming the data stream from the EPID 112 into a standard video format, the synchronization of the imager 112 and the LINAC treatment head 110 based on the different types of measurements acquired with the EPID 112, as well as data transfer, frame processing, and calibration. The controller 120 can also store and display the final image data, the dose image, as well as provide instructions for taking corrective actions. Controller 120 can include a computer with typical hardware, such as a processor, and an operating system for running various software programs and/or communication applications. The computer can include software programs that operate to communicate with the radiation treatment device 103, which software programs are operable to receive data from external software programs and hardware. The computer can also include any suitable input/output devices adapted to be accessed by medical personnel, as well as input/output (I/O) interfaces, storage devices, memory, keyboard, mouse, monitor, printers, scanner, etc. The computer can also be networked with other computers and radiation therapy systems. Both the radiation therapy device 103 and the controller 120 can communicate with a network as well as a database and servers. The controller 120 can also be configured to transfer medical image related data between different pieces of medical equipment.

The system 100 also includes a plurality of modules containing programmed instructions (e.g., as part of controller 120, or as separate modules within system 100, or integrated into other components of system 100), which instructions cause system 100 to perform different tuning, calibration, and verification functions related to the radiation treatment device 103, as discussed herein, when executed. The modules can be written in C or C++ programming languages, for example. Computer program code for carrying out operations as described herein may also be written in other programming languages.

Figure 2A:
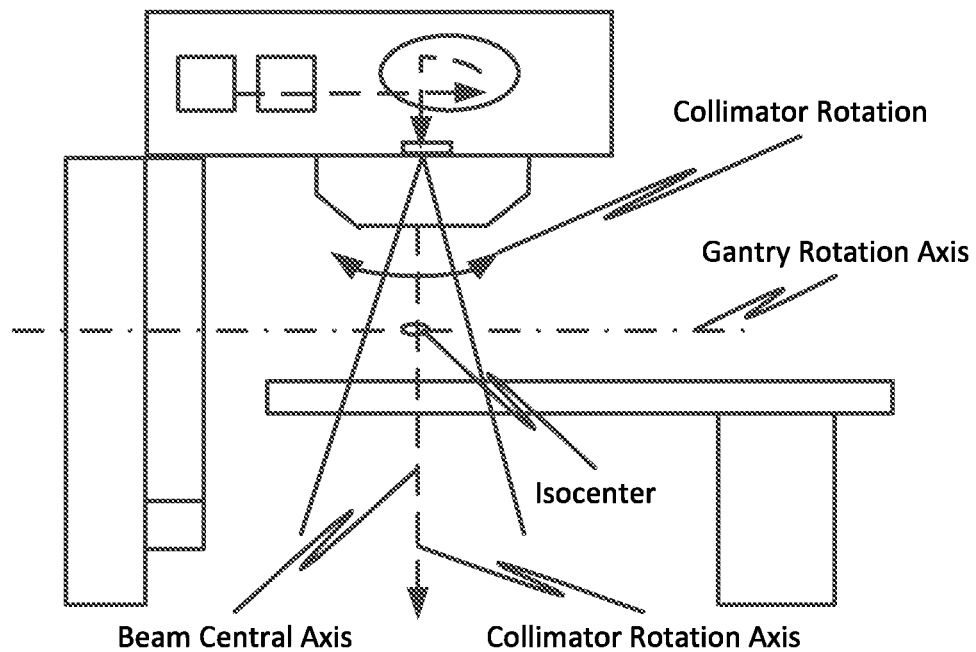
FIGS. 2A and 2B illustrate the rotation axes and coordinate frame orientation of the radiation treatment device of FIG. 1.
Figure 2B:
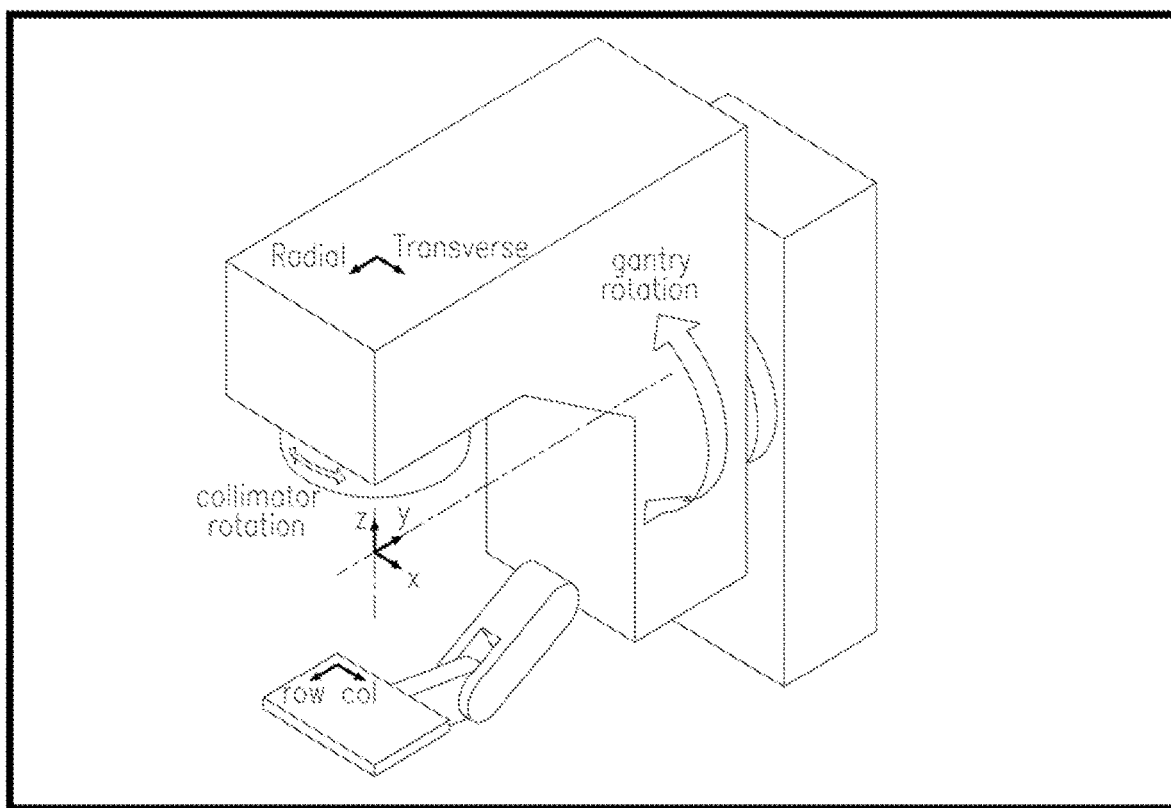

The system 100 including the EPID 112 integrated with the radiation treatment device 103 allows for all radiation detection and radiation data measurement related activities, as well as image guidance activities, such as, but not limited to, generation of scattered radiation from different points in the radiation field, generation of off axis-fields, scattering data acquisition, scattering data interpretation, EPID darkfield calibration, beam symmetry determination, asymmetry value calculation, image registration, image interpretation, EPID pixel calibration, and machine calibration to occur automatically and remotely. System 100 also allows for scattered radiation data acquisition, beam symmetry evaluation, beam asymmetry value calculation, and system calibration (i.e., data relating to gantry, collimator jaws, MLC, radiation source, EPID, X-ray target, beam steering coils, etc.). The data related to measured scattered radiation which is used to determine and evaluate different beam symmetry related parameters and characteristics of the radiation treatment device 103 can be performed using different algorithms. The determination of adjustments needed to be made in the control element outputs based on the evaluated parameters and characteristics may also be determined using different algorithms. Once the required beam characteristics are determined, the necessary tuning and/or calibration and/or verification protocols are automatically sent to the radiation treatment device 103 and the control elements are automatically or manually adjusted until their outputs fall within accepted ranges. The adjusting can also be done as a combination of automatic and manual adjustments. FIGS. 2A and 2B illustrate the radiation beam central axis, the gantry rotation axis, the collimator rotation axis, and the isocenter of system 100.

Figure 3:
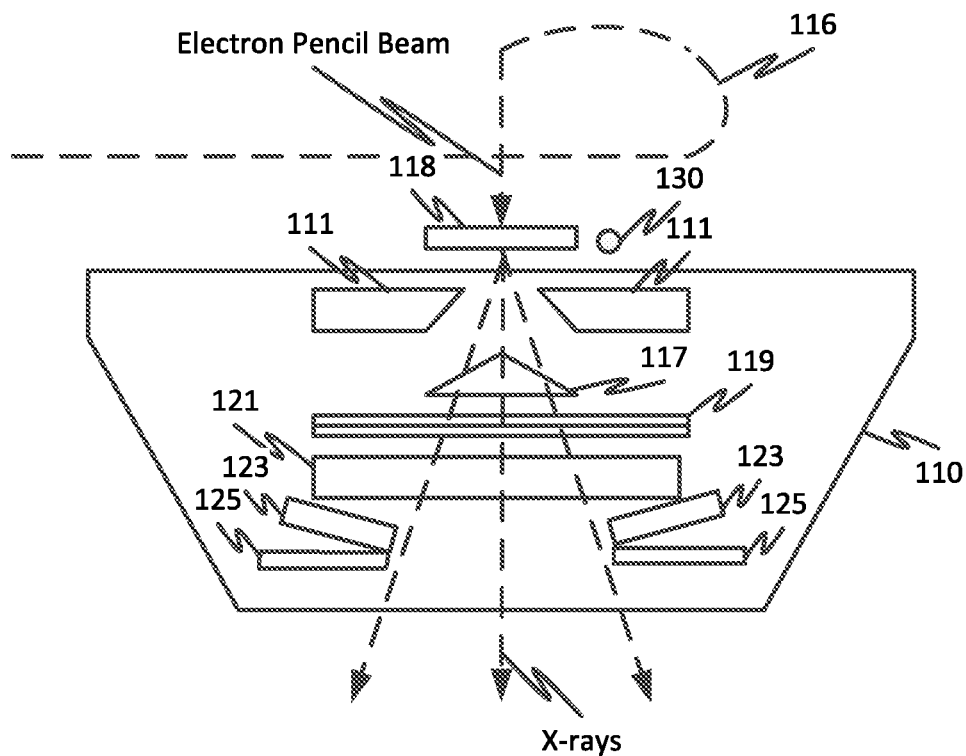
FIG. 3 illustrates a linac treatment head used in a radiation treatment system operating in a photon generation mode.

FIG. 3 illustrates a LINAC treatment head 110 when the device 103 operates in a photon mode. The LINAC treatment head 110 can include one or more retractable X-ray targets 118 where clinical photon beams, such as X-rays, are produced, one or more flattening filters (FF) 117, which can be mounted on a rotating carousel or sliding drawer for ease of mechanical positioning of the filters 117 into the X-ray or photon beam, dual transmission ionization chambers 119, a collimating device (i.e., collimator) including primary collimators 111, adjustable secondary collimators with two upper jaws 121 and two independent lower jaws 123, multileaf collimators (MLC) 125, and a field defining light source 130.

Primary collimators 111 define a maximum circular radiation field, which is then further truncated with the adjustable secondary collimators (121, 123) to produce rectangular and square fields at the LINAC isocenter. The primary collimator 111 defines the largest available circular field size and is a conical opening that can be machined into a tungsten shielding block, for example, with the sides of the conical opening projecting on to edges of the X-ray target 118 on one end of the block, and on to the flattening filters 117 on the other end. The thickness of the shielding block is usually designed to attenuate the average primary X-ray beam intensity to less than 0.1% of the initial value. Any other applicable material besides tungsten can also be used.

The secondary beam defining collimators include four blocks, two forming the upper jaws 121 and two forming the lower jaws 123. They can provide rectangular and square fields at the LINAC isocenter, with sides of the order of few millimeters up to 40 cm. Alternatively, the jaws could be independent asymmetric jaws to provide asymmetric fields, such as one half or three quarter blocked fields in which one or two beam edges are coincident with the beam central axis. The optional multileaf collimators (MLC) 125 can be made of 120 movable leaves with 0.5 cm and/or 1.0 cm leaf width, for example. For each beam direction, an optimized intensity profile is realized by sequential delivery of various subfields with optimized shapes and weights. When using MLCs, from one subfield to the next, the leaves may move with the radiation beam on (i.e., dynamic multi-leaf collimation (DMLC)) or with the radiation beam off (i.e., segmented multi-leaf collimation (SMLC)). Such an MLC system can cover fields up to 40×40 $cm^2$, for example, and can require 120 individually computer controlled motors and control circuits. Miniature versions of the MLC can also be used. For example, miniature MLCs that project 1.5-6 mm leaf widths and up to $cm^2$ fields at the LINAC isocenter, could also be used.

The ionization chamber 119 could be a dual transmission ionization chamber used for monitoring the photon radiation beam output as well as the radial and transverse beam flatness. The ionization chamber 119 acts as an internal dosimeter, and can be permanently imbedded into the LINAC treatment head 110 to continuously monitor the radiation beam output. The ionization chamber 119 could also be sealed to make its response independent of ambient temperature and pressure. The ionization chamber 119 can include a primary and a secondary ionization chamber with the primary chamber measuring monitor units (MUs). Typically, the sensitivity of the chamber electrometry circuitry is adjusted in such a way that 1 MU corresponds to a dose of 1 cGy delivered in a water of phantom at the depth of dose maximum on the central beam axis when irradiated with a 10×10 cm$^2$ field at a source to surface distance (SSD) of 100 cm. Once the operator preset number of MUs has been reached, the primary ionization chamber circuitry shuts the radiation treatment device 103 down and terminates the dose delivery to the patient 101. Before a new irradiation is initiated, the MU display is reset to zero.

In addition to monitoring the primary dose in MUs, the ionization chamber 119 can also monitor other operating parameters such as the beam energy, flatness and symmetry. Measurements of all of these additional parameters requires that the ionization chamber electrodes of the primary and secondary chambers be divided into several sectors, with the resulting signals used in automatic feedback circuits to steer the electron beam through the accelerating waveguide 115 and the beam transport system 116 and onto the X-ray target 118 or scattering foils 127, thereby ensuring consistent beam flatness and symmetry.

The LINAC treatment head 110 can also include a field defining light source 130 to provide a convenient visual method for correctly positioning the patient 101 for treatment using reference marks. The light source 130 may be mounted inside the collimator and can be positioned at the location of the X-ray target 118 by a rotating carousel or a sliding drawer assembly, or it may be positioned to one side of the collimator axis of rotation with the light reflected by a mirror. In clinical operations, the light field illuminates an area that coincides with the radiation treatment field on the patient's skin and the alignment of the light field with the skin marks on the patient is used as the final confirmation that the patient 101 is correctly positioned with respect to the radiation beam.

Figure 4:
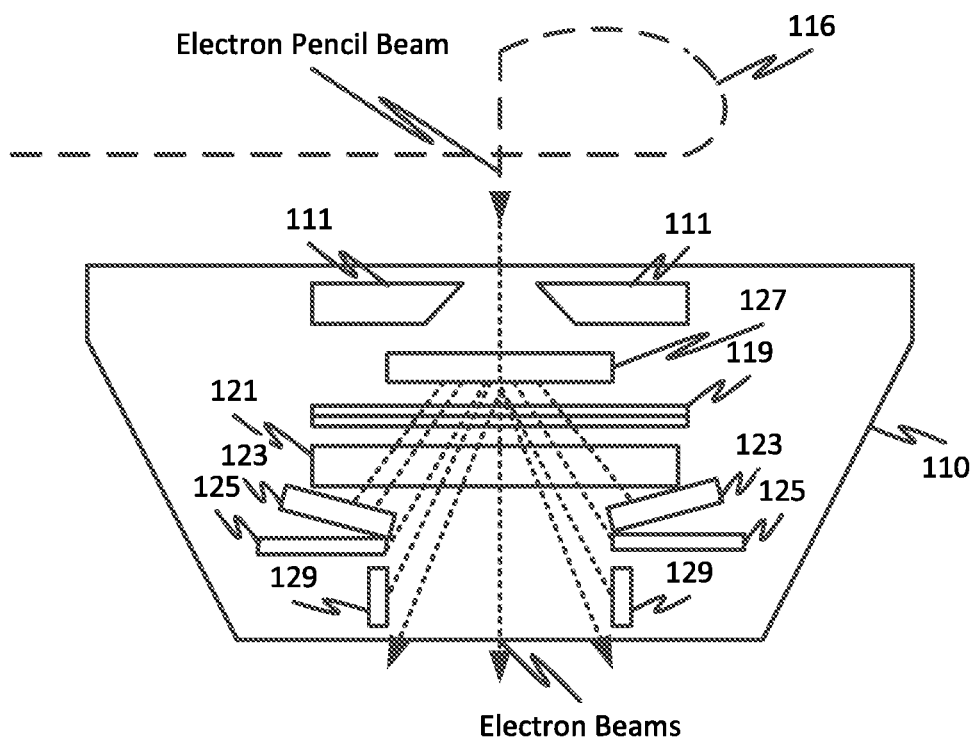
FIG. 4 illustrates a linac treatment head used in a radiation treatment system operating in an electron-beam generation mode.

When the radiation treatment device 103 operates in an electron-beam mode, the LINAC treatment head 110 does not need the X-ray target 118 and the flattening filters 117. FIG. 4 illustrates a LINAC treatment head 110 when the radiation treatment device 103 operates in the electron-beam mode. To activate an electron-beam mode, both the X-ray target 118 and the flattening filters 117 used in the photon mode are removed from the electron pencil beam path. The electron pencil beam exits the beam accelerator module 108 through a thin window (not shown) usually made of beryllium, which minimizes the pencil beam scattering and bremsstrahlung production. To produce clinical electron beams from the electron pencil beams, thin scattering foils 127 of a high atomic number (copper or lead, for example) are positioned into the electron pencil beam at the level of the flattening filters 117 in the X-ray mode. In addition to the primary 111 and secondary collimators 121, 123, the clinical electron beams also rely on electron beam applicators (cones) 129 for beam collimation. The rest of the collimation and beam shaping elements are the same as in the photon-beam mode.

Figure 5A:
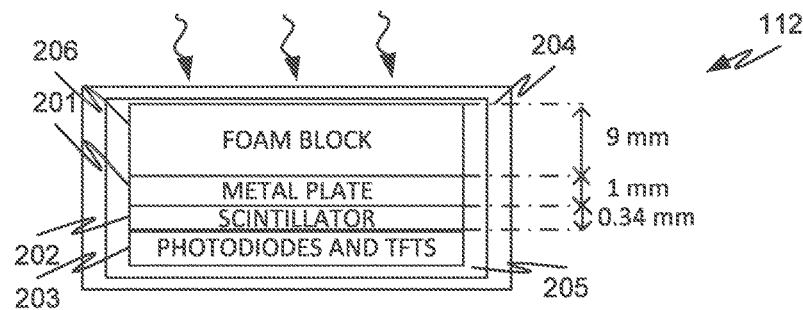
FIGS. 5A-5B illustrate an exemplary imaging device used in the radiation treatment device of FIG. 1.
Figure 5B:
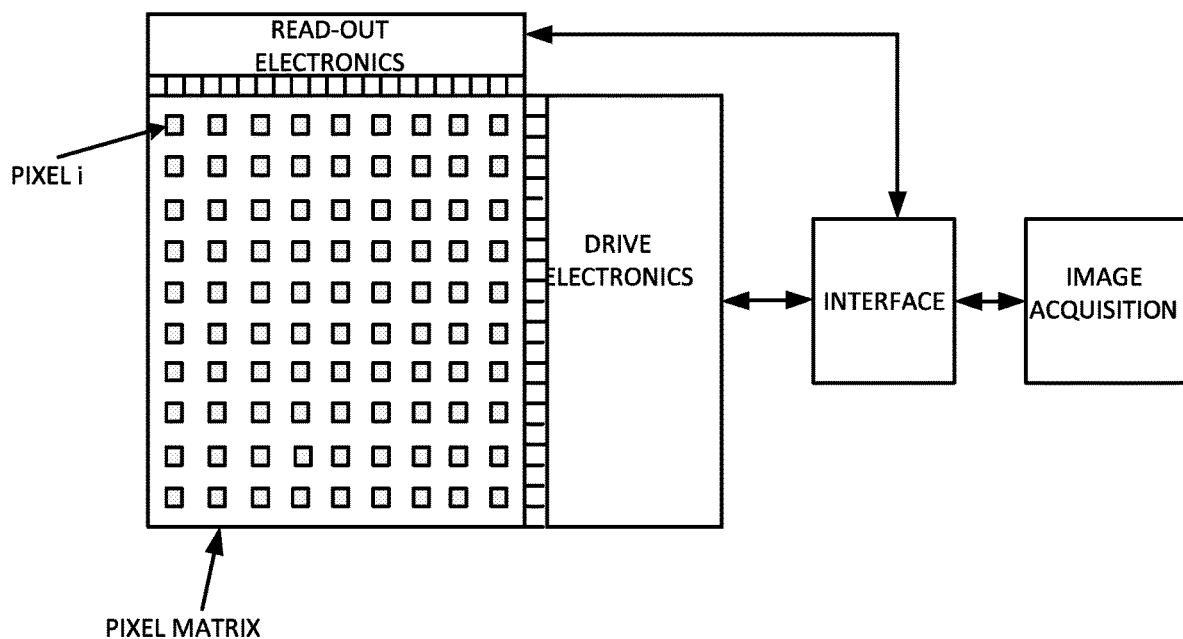

FIGS. 5A-5B illustrate an exemplary EPID 112 used to generate EPID images and scattered radiation data. The EPID 112 could be an amorphous silicon type detector panel including a 1 mm copper plate 201 to provide build-up and absorb scattered radiation, and a scintillating phosphor screen 202 made of terbium doped gadolinium oxysulphide to convert the incident radiation to optical photons. The scintillating screen 202 can have a thickness of 0.34 mm, for example. The EPID 112 can also include a pixel matrix 203 created from an array of 1024×768 or 1280×1280 pixels i, where each pixel i is made up of a photodiode to integrate the incoming light and a thin film transistor (TFT) to act as a three-terminal switch for readout. The EPID 112 can also include electronics to read out the charge from the transistor and translate it into an image data.

The imager 112 can also be enclosed in a protective plastic cover 204 with an air gap 205 between the protective cover 204 and the copper plate 201. Alternatively, layers of foam and paper 206 can be included between the protective cover 204 and the copper plate 201. The protective cover can be about 3 cm above the effective point of measurement. The buildup at the active matrix can be equivalent to 8 mm of water, which means that the dose maximum has not been reached for either of the energies of the device 103. The EPID can be positioned at source to EPID distances (SDD) from 95 cm to 180 cm. It can also have an active imaging area of 40×30 cm$^2$ or 43×43 cm$^2$, for example. The maximum frame acquisition rate can be 15 frames/second, the permitted dose range can be between 4-25 MV, and the permitted dose rates can be between 50-600 MU/min, for example. The disclosed EPID 112 is, however, only exemplary, and any other applicable EPIDs can be used as the measuring device 112.

EPID as Beam (A)symmetry Determination Device

A requirement in radiation therapy is that the radiation dose variation over the targeted volume (i.e., tumor site, for example) is limited so that all points in the targeted volume receive the prescribed radiation dose within a tolerance range. One of the factors that influences radiation dose variation is radiation beam symmetry. Radiation beam symmetry is defined as the maximum ratio of radiation doses at two symmetric points relative to the radiation beam center as it is projected from the radiation source past the radiation limiting devices (primary collimators 111, collimator jaws 121, 123, MLC 125, and/or cones 129) to the isoplane. When the radiation beam is symmetric, two symmetric points relative to the radiation beam center are exposed to the same radiation dose. The more symmetric the radiation beam, the less dose variation is present in the targeted volume.

Figure 6:
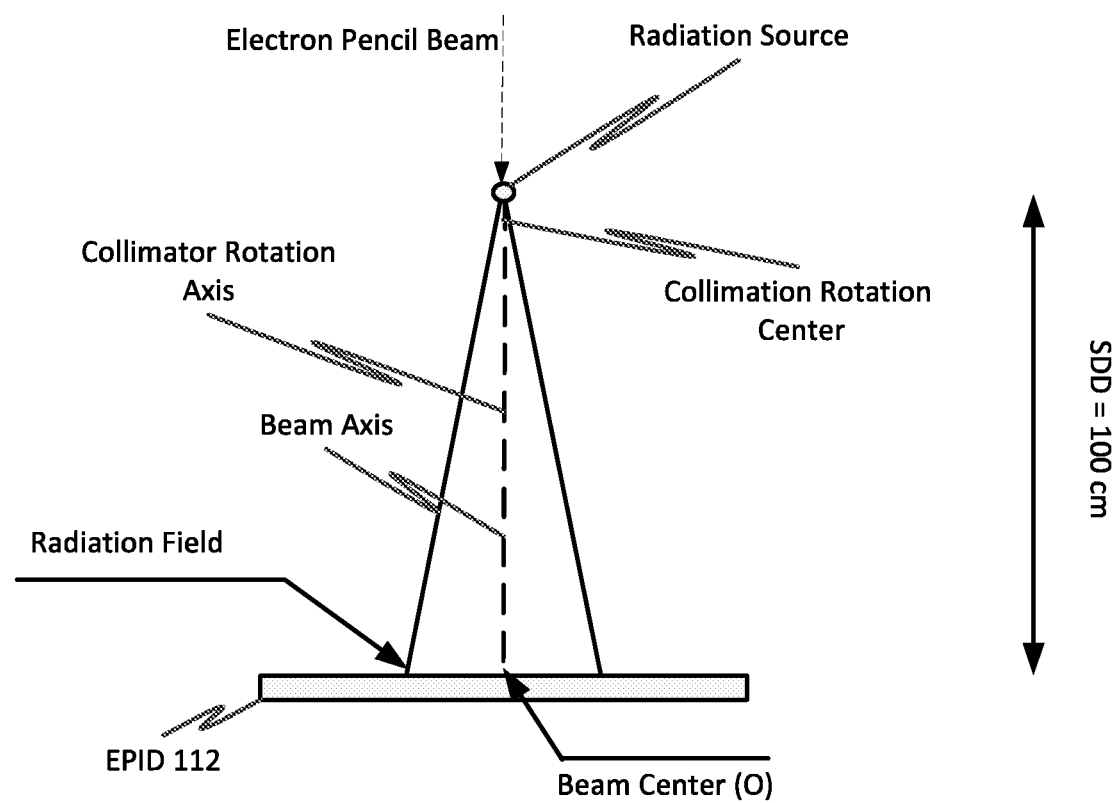
FIG. 6 illustrates a correlation between the beam center, collimator rotation axis, collimator rotation center, and a radiation source for an exemplary embodiment using an EPID.
Figure 7:
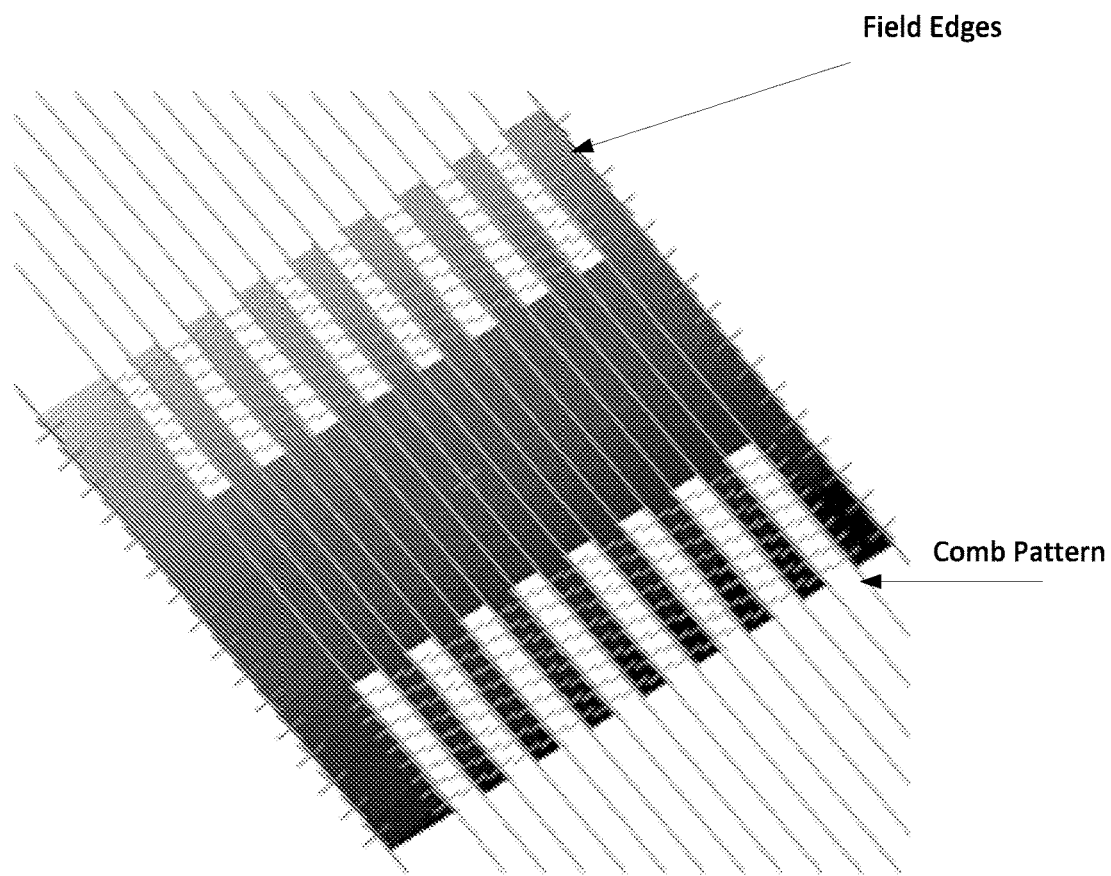
FIG. 7 illustrates field edges and comb patterns formed by a collimator used in the radiation treatment device of FIG. 1.
Figure 8:
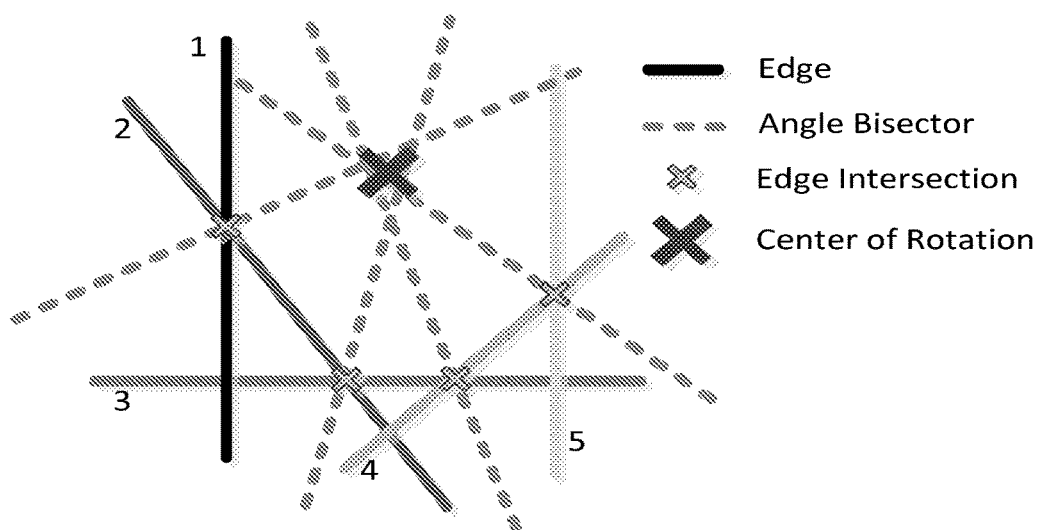
FIG. 8 illustrates an example of how the detected edges at different collimator angles are combined according to an exemplary embodiment.

The radiation beam center (O) is defined as the collimation rotation center at a certain height SDD projected from the radiation source onto the imaging plane, as shown in FIG. 6. The collimation rotation center can be calculated many different ways, including, by taking a plurality of images (five, for example) with the collimator MLC rotating, and calculating the collimation rotation center from the set of (five) images obtained. Generally, the MLC jaws or leaves at a first height form a comb pattern, and the MLC jaws or leaves at a second, different height are used to shape the left/right field edges as shown in FIG. 7. In order to determine the collimation rotation center, the detected edges at different collimator angles are combined as shown in FIG. 8, for example. For each pair of subsequent edges, the angle bisector line is calculated. This results in four angle bisectors. Ideally, this set of lines intersects at the center of rotation. A least squares approach is then applied for finding the point in space with the least distance to all bisection lines. This point in space is the beam center O. This beam center determination method is only exemplary, and any other beam center determination method can be applied.

If the radiation source is at the collimation rotation center as shown in FIG. 6, the radiation beam axis coincides with the collimator rotation axis, and the beam center O is independent of the height of the collimation element used to determine the center. If not, the beam center O is determined based on the difference between the source position and the collimation rotation axis. Beam symmetry is considered along both the X-axis and the Y-axis, with the Z axis being from the radiation source to the isoplane, and the Y axis increasing from the center toward the gantry stand structure, as shown in FIGS. 2A and 2B.

Figure 9:
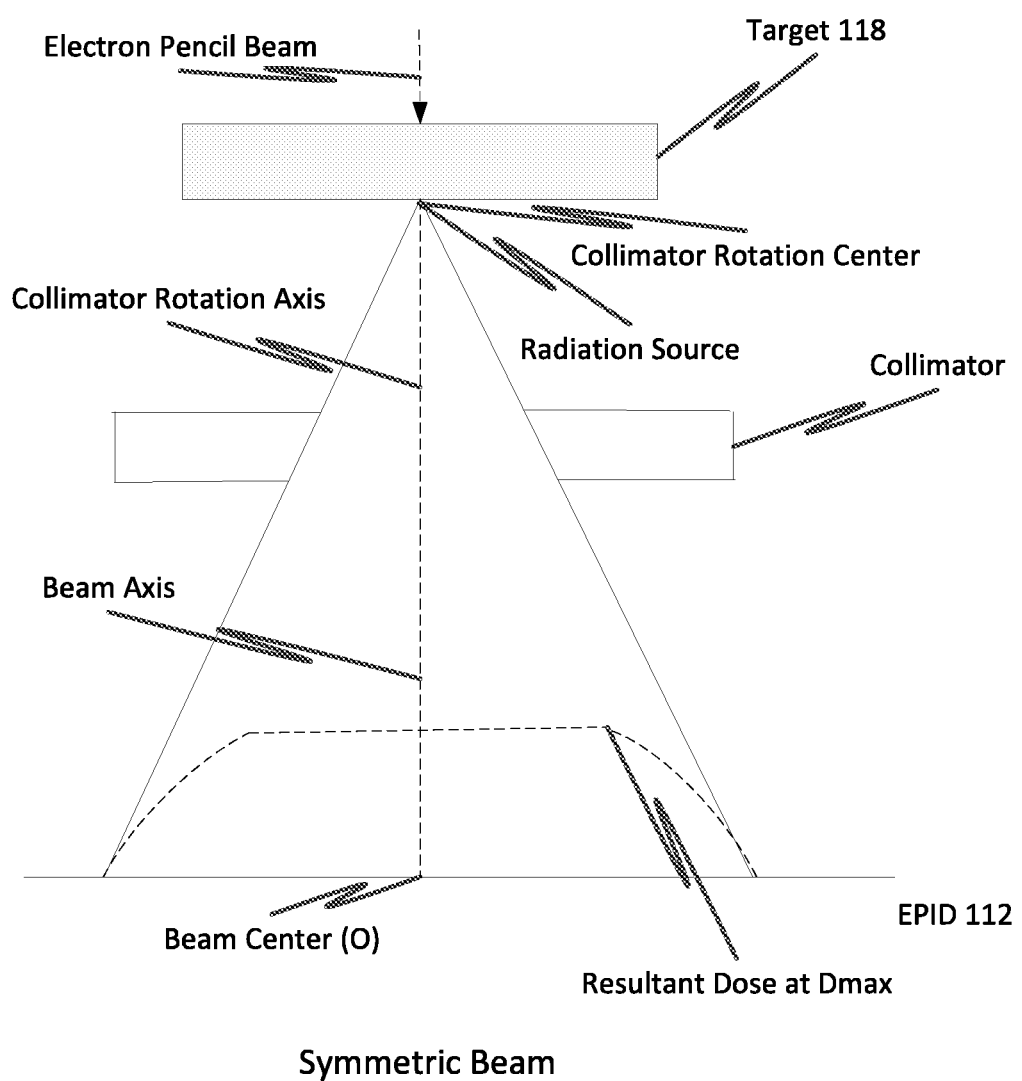
FIG. 9 illustrates an example of a symmetric beam.
Figure 10:
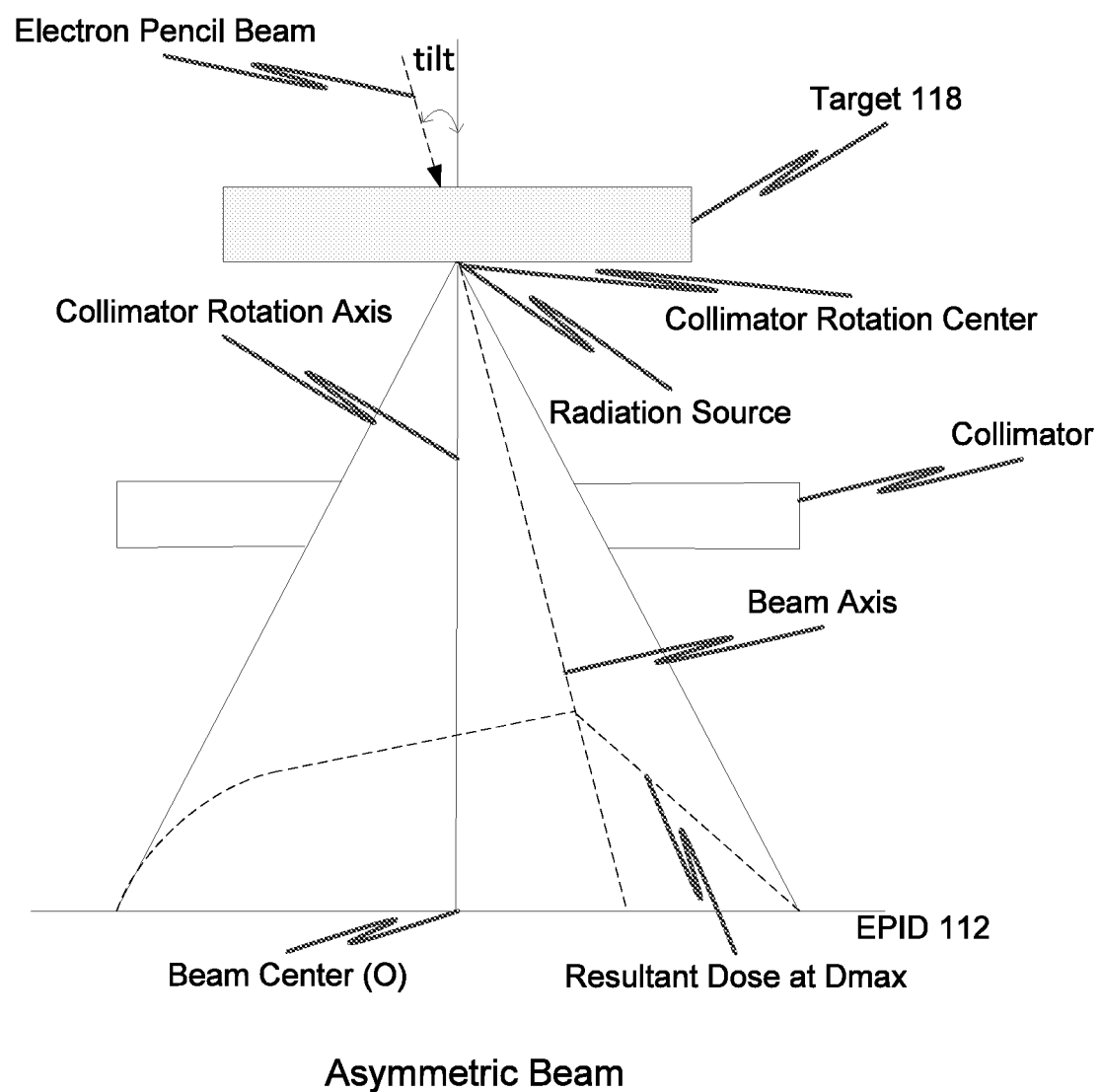
FIG. 10 illustrates an asymmetric beam obtained from a tilt of the radiation source.

Depending on the radiation treatment system, there are many sources causing a radiation beam not to be symmetric (i.e., asymmetric radiation beam). For example, if the electron pencil beam hits the target 118 (in radial and transverse planes) so that the radiation source position coincides with the collimation rotation center, the resultant radiation beam is symmetric relative to the radiation beam center O, as shown in FIG. 9. However, if the electron pencil beam hits the target 118 as shown in FIG. 10, namely, the electron pencil beam is tilted relative to the collimator rotation axis, the radiation source will generate asymmetries in the radiation beam.

As previously discussed, EPIDs have been previously used to determine beam symmetries. Such measurements, however, required that the EPIDs be calibrated using complex calibration algorithms to offset the effects that energy fluence, beam field size, dose rate, and photon energy has on the EPID pixel values.

Figure 11:
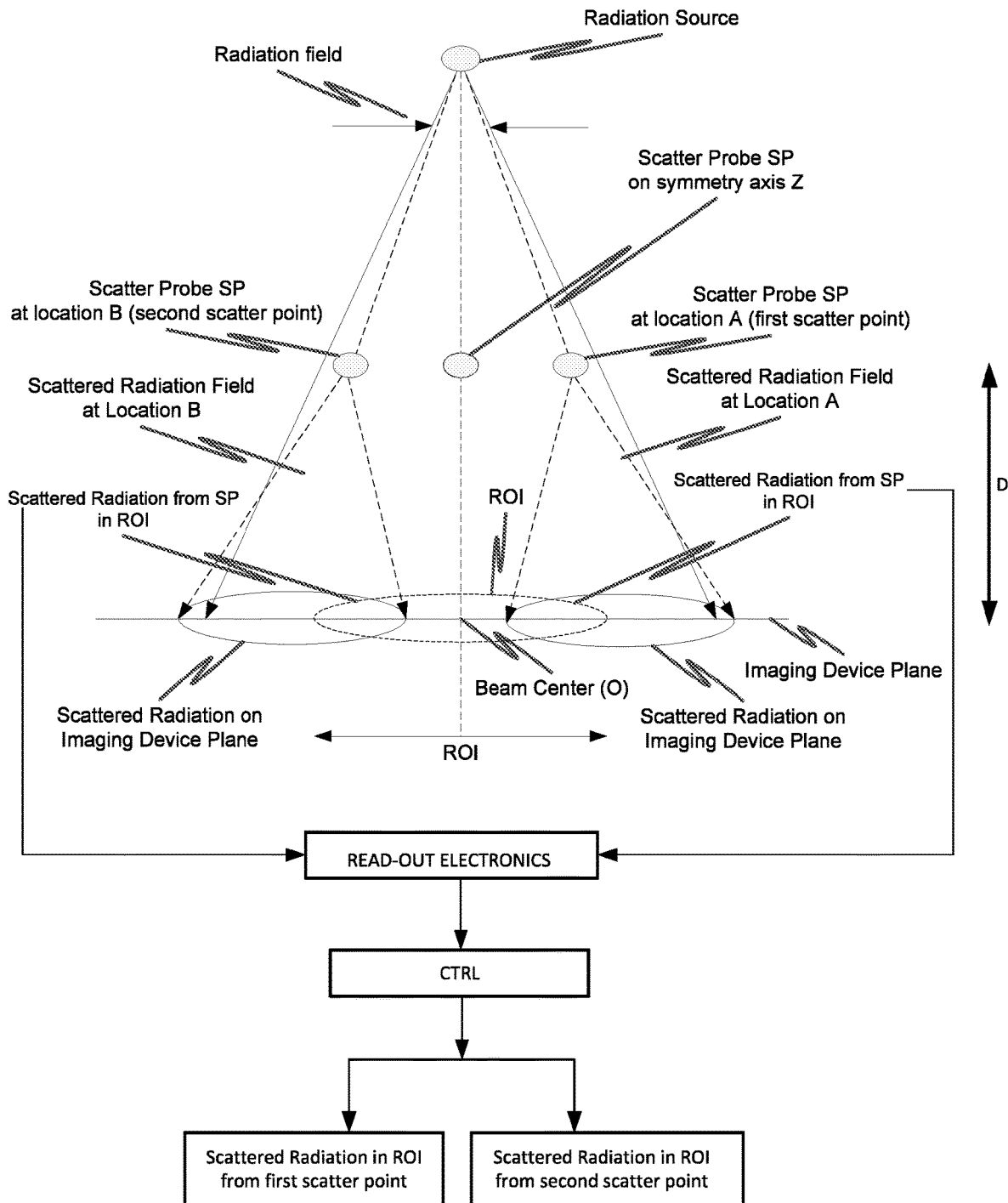
FIG. 11 illustrates different positions of a scattering probe in the radiation field.
Figure 12:
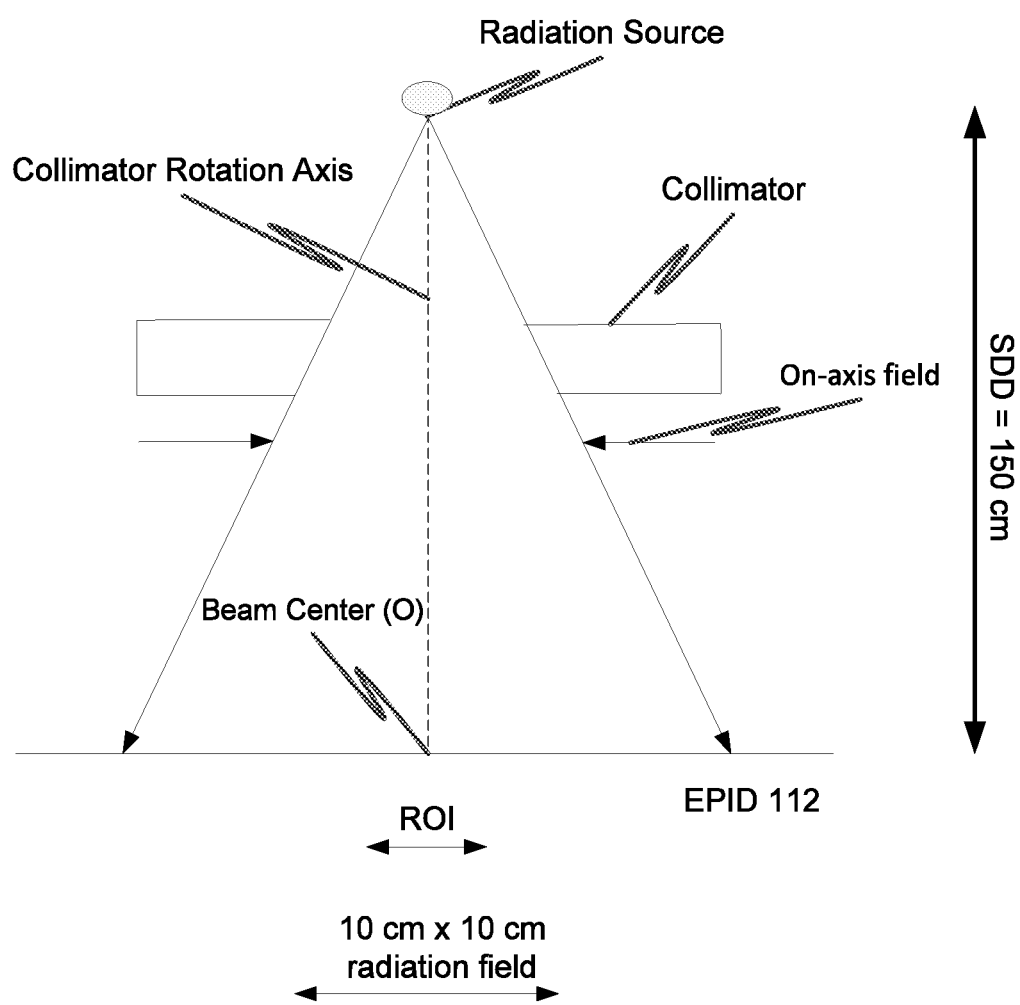
FIG. 12 illustrates a region of interest ROI around a beam center for a radiation field according to an exemplary embodiment.
Figure 13:
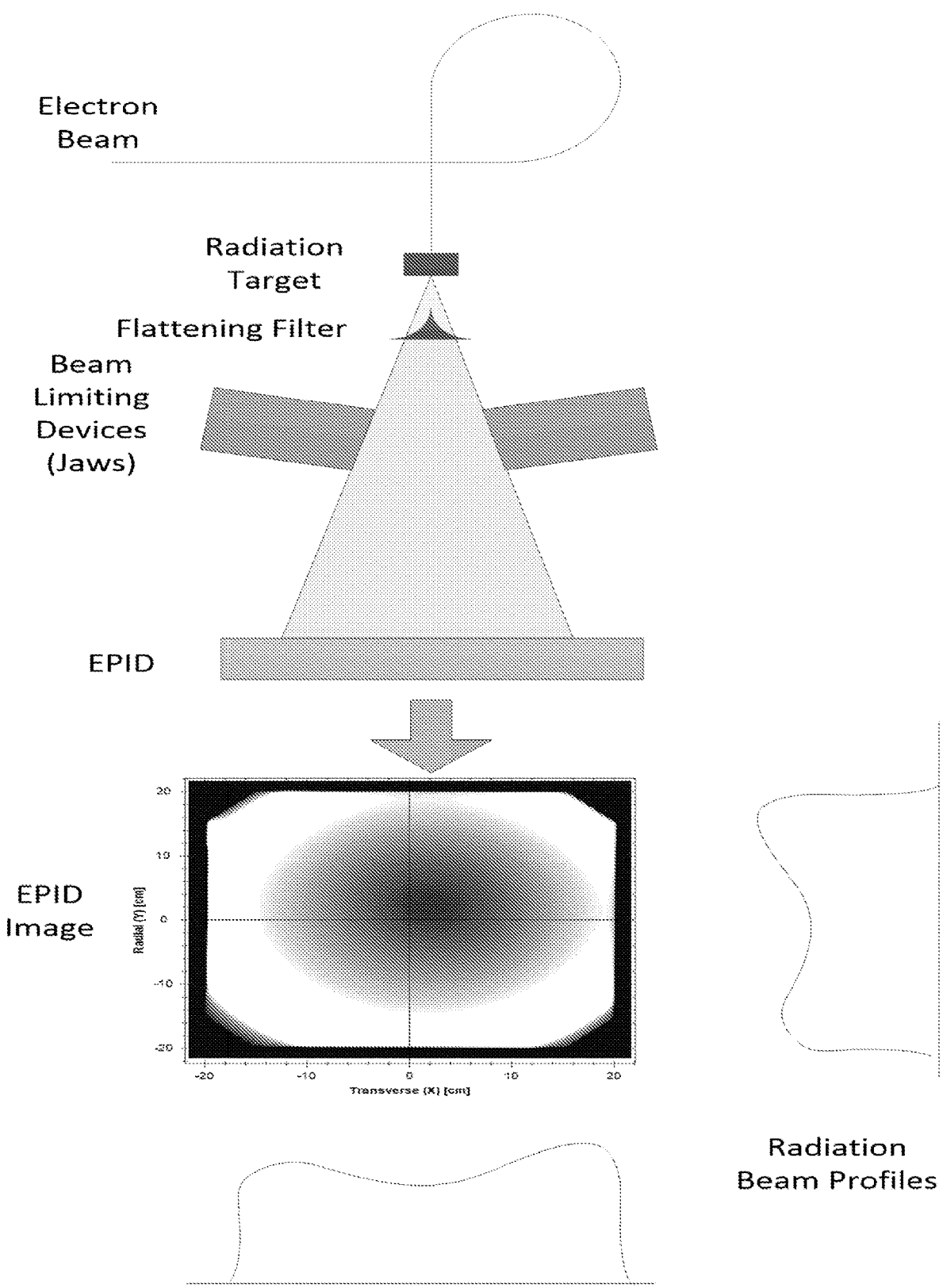
FIG. 13 illustrates an exemplary radiation beam profile generated by a radiation beam.

In the present disclosure, systems and methods are provided that allow EPIDs to be used to determine beam symmetries in a radiation treatment system 100 (regardless of whether flattening filters FF 117 are used or not) without having to calibrate the EPID utilizing elaborate calibration protocols. This can be done by generating scattered radiation at different locations in the radiation field using a scatter probe SP, as shown in FIGS. 11 and 12, measuring the scattered radiation from the different scatter probe SP locations, and evaluating the scattered radiation obtained from scatter locations (scatter points) which are symmetrically opposed to each other with respect to the collimator rotation axis (locations A, B, for example) using the same region of interest ROI of the EPID 112 by comparing the measured scattered radiations.

If the beam is symmetric, the amount of scattered radiation measured by the pixels in a predetermined ROI from scatter points which are symmetrically opposed to each other relative to the collimator rotation axis, should be the same.

If the beam is not symmetric, the amount of scattered radiation measured by the pixels in the same ROI from the symmetrically opposing scatter points will be different. Since the comparing is between the same pixels in the same ROI, the correlation between the measurements only depends on the constancy of the EPID sensitivity within the ROI and not the actual pixel sensitivity values. Thus, a calibration of the EPID 112 to determine actual pixel sensitivities is not needed for determining beam symmetry.

In order to generate scattered radiation at different locations in the radiation field in a radiation treatment system 100, a small off-axis field is generated and moved in a radially symmetric fashion around the collimator rotation axis by rotating the collimator around the collimator rotation axis from a first location to a plurality of subsequent locations within its 360-degree rotational angle. By irradiating the small off-axis field at different collimator locations, scattered radiation is obtained from different locations in the radiation field. By evaluating the scattered radiation generated from symmetrically opposite locations in the radiation field with respect to the collimator rotation axis, the beam symmetry can be evaluated.

In order to obtain scattered radiation from symmetrically opposite locations, in an exemplary embodiment shown in FIGS. 13, 14, 14A and 14B, the collimator is rotated from a first collimator location to a second collimator location, which is 180 degrees from the first location, for example, whereby the scatter probe SP, and thus, the location of the small off-axis field, is moved from a first location to a symmetrically opposite location with respect to the collimator rotation axis. By evaluating the scattered radiation measured in a predetermined region of interest ROI of the EPID 112 when the collimator is in the first location against the scattered radiation measured using the same region of interest ROI of the EPID 112 when the collimator is in the second location, the beam symmetry can be evaluated.

Figure 14:
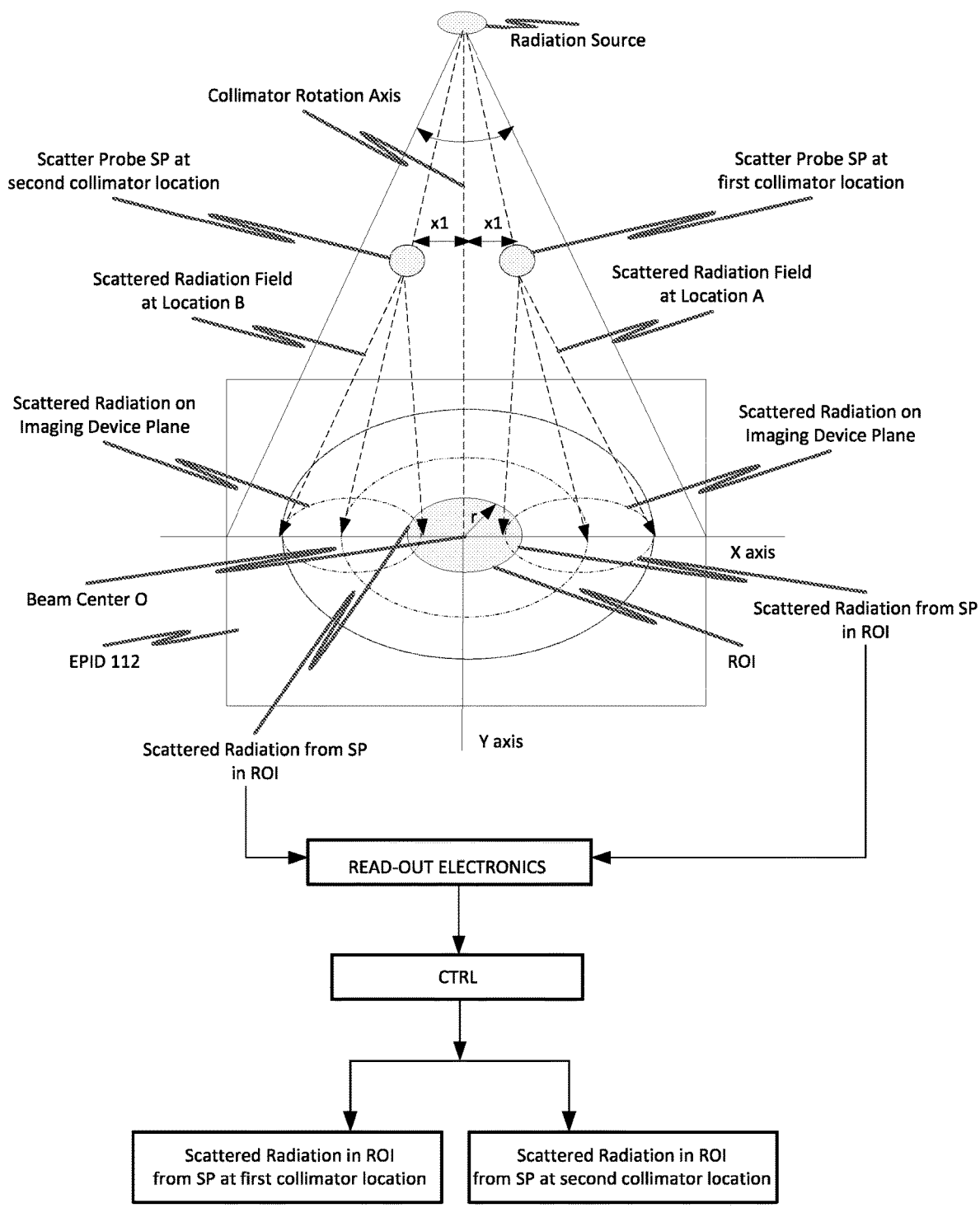
FIGS. 14, 14A and 14B illustrate two-dimensional angular scattered radiation intensity distributions around the radiation beam center according to different exemplary embodiments.
Figure 14A:
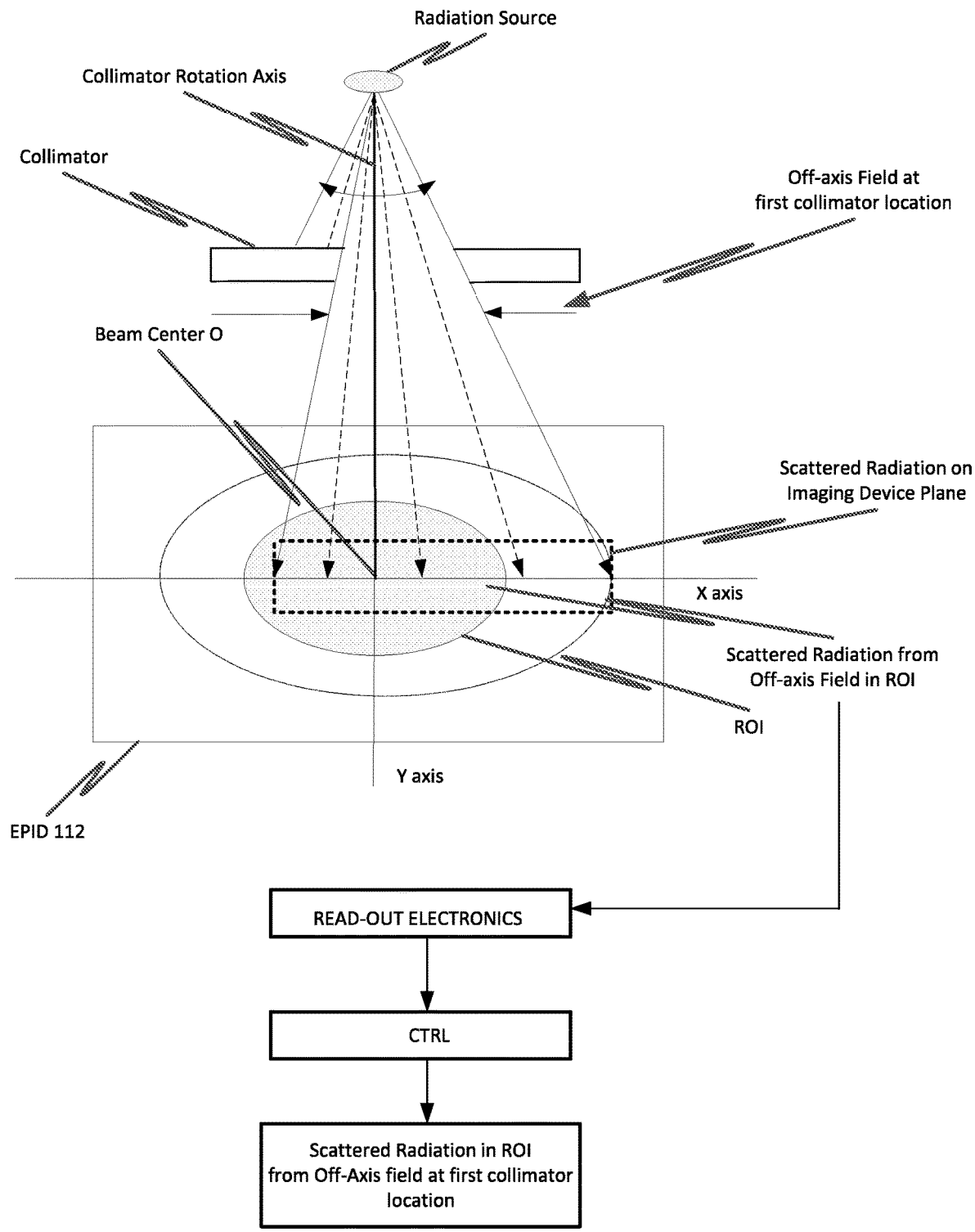
Figure 14B:
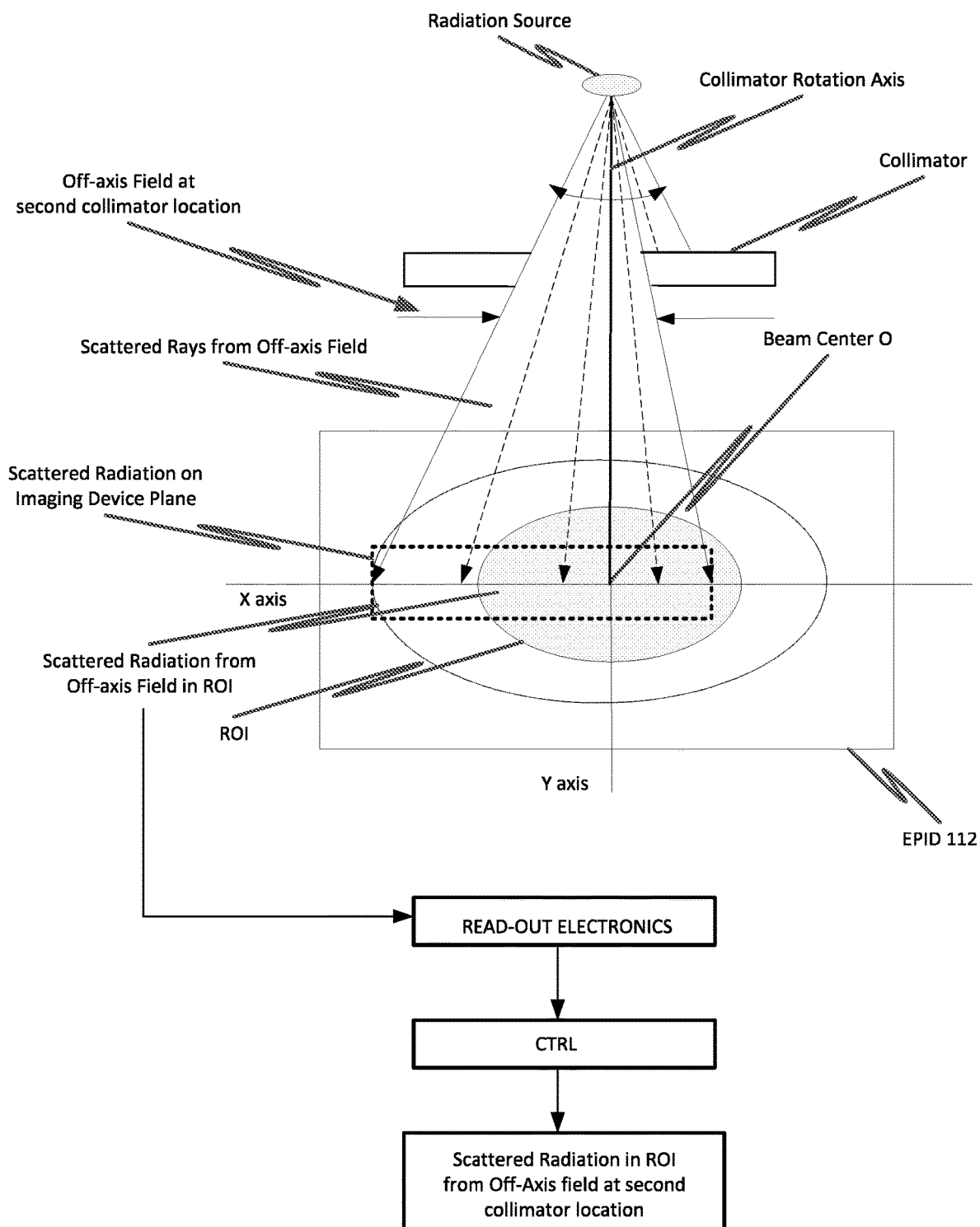

In order to make scatter measurements independent of asymmetries due to the geometric collimation imperfections and the amount of collimator rotation, the predetermined ROI is a circular region of interest centered around the projection of the collimator axis of rotation on the EPID 112 (i.e., around the beam center O), as shown in FIGS. 12-14, 14A and 14B. FIGS. 14, 14A and 14B also show two-dimensional angular scattered radiation intensity distributions obtained around the radiation beam center O on the EPID 112 plane for such a setup.

By measuring the amount of scattered radiation when the collimator is positioned at a first location using the pixels of the EPID 112 that are located in a circular region of interest ROI around the beam center O, and comparing it to the amount of scattered radiation measured by the same pixels in the same ROI of the EPID 112 when the collimator is positioned at a second location, which is 180 degrees from the first location, for example, the radiation beam symmetry can be evaluated. If the measured scattered radiation in the ROI at the first collimator location is the same as the measured scattered radiation in the same ROI at the second collimator location, the radiation beam is symmetric, as shown in FIG. 9. If the scattered radiations are not the same, the beam is not symmetric.

The amount of beam asymmetry can be determined based on the difference between the measured scattered radiations for the two collimator locations. The asymmetry value can further be correlated to the tilt of the electron beam with respect to the collimator rotation axis.

Figure 15A:
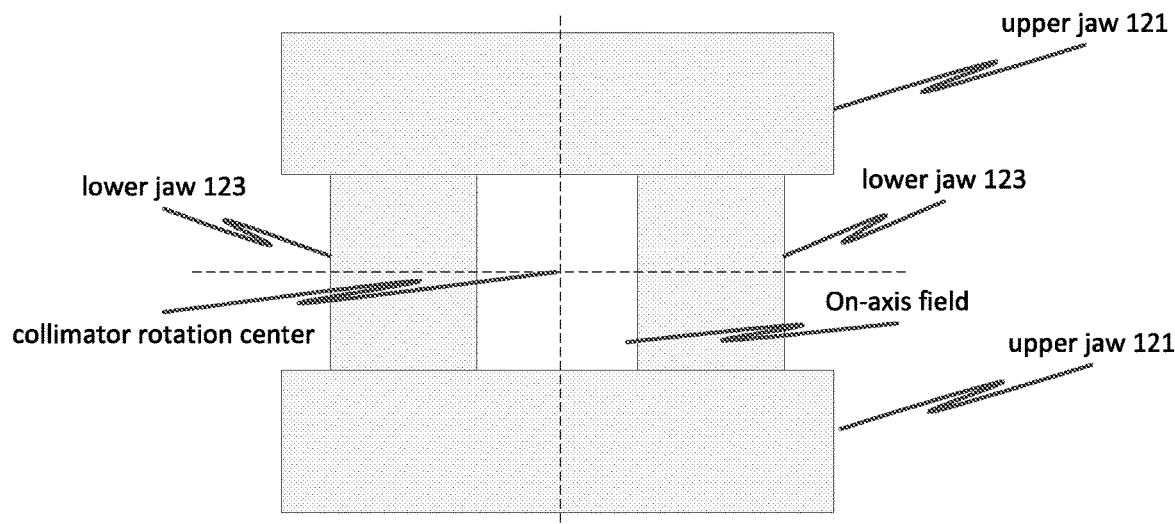
FIG. 15A illustrates positions of the collimator jaws for a symmetric radiation field, according to an exemplary embodiment.
Figure 15B:
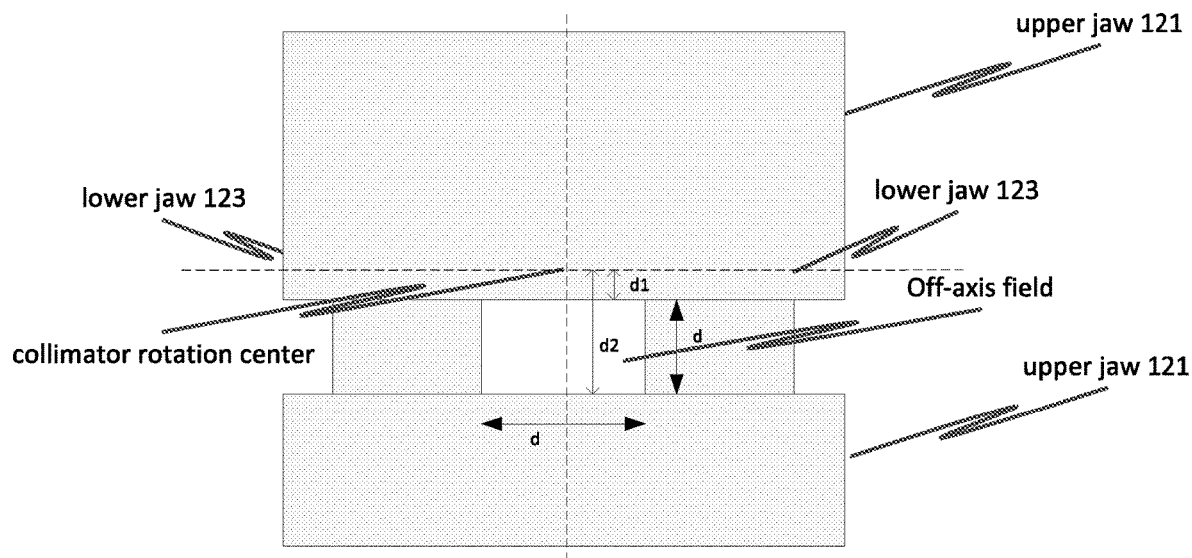
FIG. 15B illustrates positions of the collimator jaws for generating a small off-axis field according to an exemplary embodiment.

There are numerous ways to generate a small off-axis field in the radiation treatment system 100. In an exemplary embodiment, in a radiation treatment system 100 with a 10 cm×10 cm radiation field for example, a small (i.e., 1-2 cm, for example) off-axis field can be generated by positioning the upper jaws 121 and the lower jaws 123 of the collimator in specific locations relative to each other and relative to the collimator rotation center. For example, in their original positions, both the upper jaws 121 and the lower jaws 123 are positioned so as to be symmetric around the collimator rotation center and thus around the collimator rotation axis as shown in FIG. 15A. By moving the upper jaws 121 of the collimator off-center (i.e., away from the collimator rotation center) so as to be offset by a first and a second distance $d_1$, $d_2$, respectively, while the lower jaws 123 are positioned symmetrically around the collimator rotation center, and thus around the collimator rotation axis, a small square or rectangular radiation field is generated through the exposed collimator aperture, as shown in FIG. 15B. For a 10 cm×10 cm radiation field, the off-center distances $d_1$, $d_2$ could be for example, 1.5 cm and 3.5 cm, respectively. This will generate a 1 cm×1 cm off-axis field (i.e., d cm×d cm). However, the off-center distances of the upper jaws 121 as well as the sizes of the generated off-axis fields are only exemplary and any other off-center distances can be used to generate different off-axis fields.

After the upper and lower collimator jaws 121, 123 are in place to generate the small off-axis field, and without a patient, the collimator is irradiated with the radiation beam, and the EPID 112 collects and records the plurality of radiation intensity values, one for each pixel, and supplies the corresponding signals to a processing circuit for further processing. The processing circuit could be included in the EPID read-out electronics, the EPID image acquisition circuit, and/or could be part of the controller 120. Then, the collimator is rotated by 180 degrees, for example, from its initial first position i to a second position j. The second position does not have to be 180 degrees from its original first position, and instead could be any other location within its 360-degree angle rotation. When in its second position j, the collimator is again irradiated with the radiation beam, and the EPID 112 again collects and records the plurality of radiation intensity values, one for each pixel, and supplies the corresponding signals to the processing circuit for further processing.

The processing circuit is programmed to process the intensity values collected at each EPID pixel and calculate a corresponding scattered radiation amplitude value (p) for each collimator location. The processing circuit is also programmed to select particular pixels of the EPID for further processing. For example, the processing circuit is programmed to select the pixels of a particular region of interest ROI of the EPID 112 for the further processing.

In an exemplary embodiment, the processing circuit is programmed to select the pixels of a predetermined region of interest ROI of the EPID 112 that is circularly symmetric around the beam center (O) on the imaging plane of the EPID 112 for further processing. The circularly symmetric ROI can have a radius r that is equivalent to 10 pixels of the EPID 112, for example, as shown in FIG. 14. However, this ROI size is exemplary only and any other ROI size can be used. The scattered radiation amplitude value $p_i$ for the first collimator location i is then calculated by adding the intensity values collected for the pixels of the EPID 112 that are located in the selected ROI. The scattered radiation amplitude value $p_j$ for the second collimator location j is calculated by adding the intensity values collected for the pixels of the EPID 112 that are located in the same ROI as the one used for calculating the scattered radiation amplitude value $p_j$. If necessary, a normalization step can be added to take into account variations of the total beam output between the measurement at the first collimator location i and the second collimator location j.

The processing circuit is further programmed to compare the scattered radiation amplitudes $p_i$ and $p_j$ and determine, based on this comparison, whether the radiation beam is symmetric relative to the beam center O, and thus relative to the collimator rotation axis. If the scattered radiation amplitude $p_i$ is the same as the scattered radiation amplitude $p_j$, the processing circuit concludes that the beam is symmetric.

The processing circuit is further programmed to determine asymmetries defined by the measured radiation intensity values by analyzing the scattering amplitude values $p_i$ and $p_j$. By comparing the scattered radiation $p_i$ obtained at the first collimator position i to the scattered radiation $p_j$ measured when the collimator is in the second location j, an asymmetry value $A_{ij}$, representing the radiation beam offset from the collimator rotation axis is obtained from:

$$A_{ij}=(p_i-p_j)/(p_i+p_j)$$

The processing circuit is further programmed to correlate the measured asymmetry value $A_{ij}$ with the electron pencil beam tilt angle.

Figure 16:
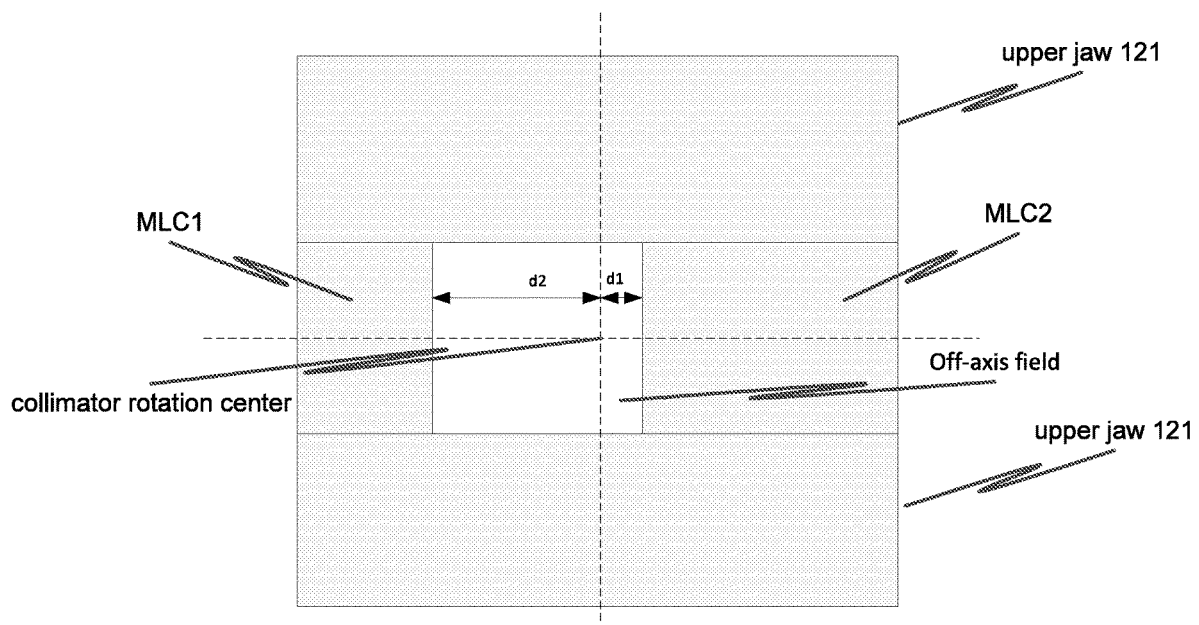
FIG. 16 illustrates positions of the collimator jaws and MLC for generating a small off-axis field according to an exemplary embodiment.

In alternative embodiments, the small off-axis fields can be generated by positioning the MLCs 125 off-center by a first and a second distance $d_1$, $d_2$, respectively, while the upper jaws 121 are positioned symmetrically around the collimator rotation axis as shown in FIG. 16. The particular ways described herein to generate small off-axis fields are not limiting, however, and any other available and applicable methods are contemplated herein.

In alternative embodiments, the EPID 112 can be exposed to basic offset (i.e., dark field) calibration prior to being used to measure the scattered radiation.

In alternative embodiments, regions of interest ROI of the EPID 112 that are not centered at the beam center O can be used to determine beam asymmetries. In such embodiments, however, the ROIs used need to be symmetric to each other with respect to the collimator rotation axis.

Figure 17:
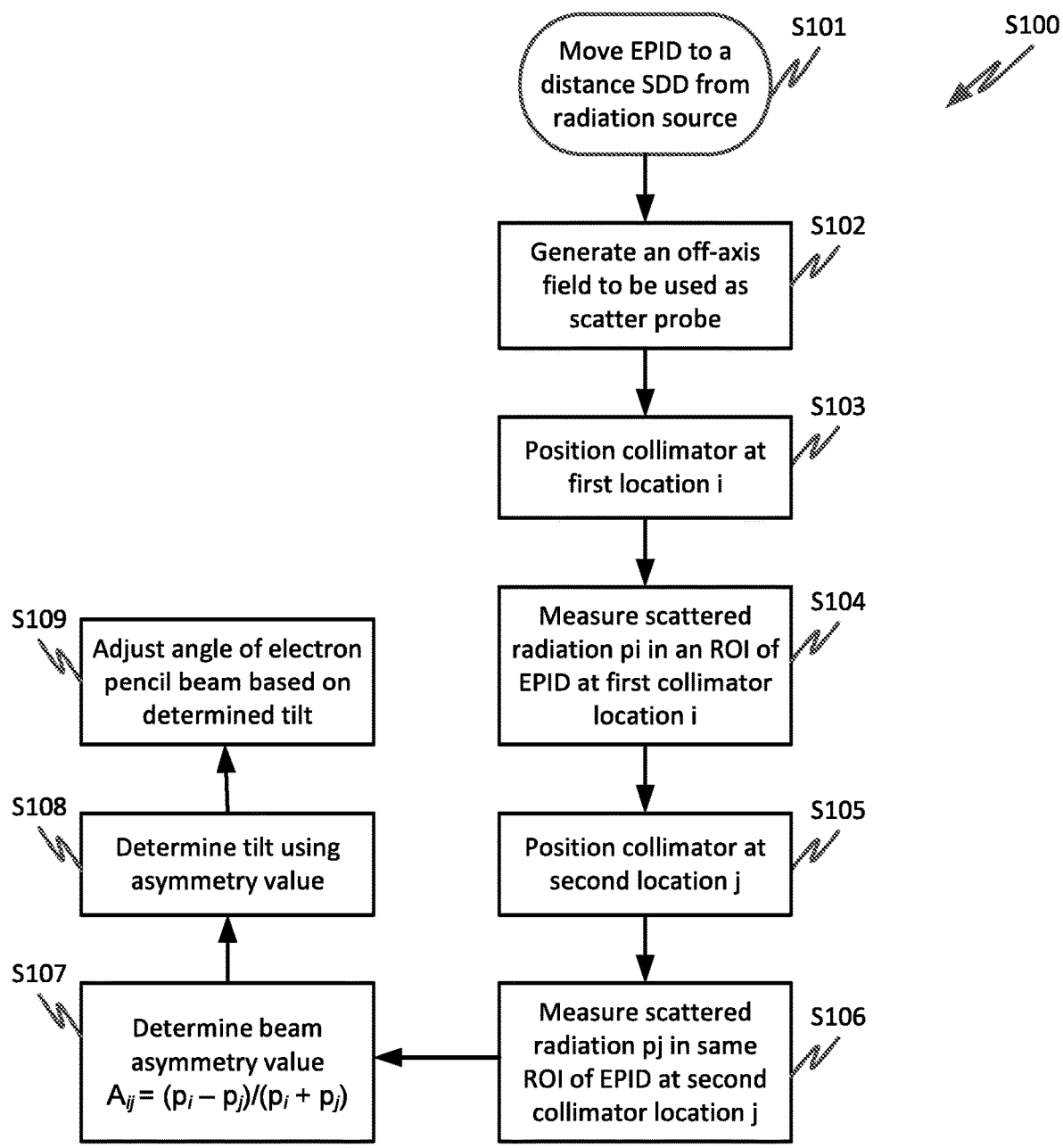
FIG. 17 illustrates an exemplary flow diagram for adjusting radiation tilt based on determined beam asymmetry using an EPID according to an embodiment.

An exemplary process S100 by which an EPID 112, which is only calibrated for basic offsets, is used to determine radiation beam asymmetry in the radiation treatment system 100, can be implemented as shown in FIG. 17. In Step S101, the EPID 112 is moved to a known distance SDD from the radiation source so as to be aligned on the propagation direction (Z axis) of the radiation beam, namely, the radiation beam axis. The distance SDD could be anywhere from 95 to 180 cm, for example. In Step S102, a small off-axis field is generated in the system 100. The small off-axis field can be generated by moving the collimator jaws 121, 123 and/or the MLC 125 a specific distance from the collimator rotation axis so as to together generate a small off-axis field through the collimator aperture. After the upper and lower collimator jaws are in place, the collimator is irradiated with the radiation beam, or the collimator is moved to a first location first and then irradiated with the radiation beam (S103), and the EPID 112 measures the radiation impinging on its surface in S104. The sum of the values captured by the pixels of the EPID 112 which are located in a specific region of interest ROI of the EPID 112, the ROI being circularly symmetric around the beam center O (the beam center O representing the projection of the collimator axis of rotation on the imaging plane of the EPID 112) and having a specific radius r, are recorded as the scattered radiation $p_i$ obtained at the first collimator location i in S104. The collimator is next rotated to a second collimator location j(S105), and in step S106, the sum of the values captured by the pixels of the EPID 112 which are located in the same region of interest ROI of the EPID 112 as used to record the scattered radiation $p_i$ obtained at the first collimator location i, are recorded as the scattering radiation $p_j$ obtained at the second collimator location j. The second collimator location is such that the off-axis field is moved to a symmetrically opposing second location from the first location relative to the collimator rotation axis.

The two values $p_i$ and $p_j$ are then compared to each other. In step S107, an asymmetry value $A_{ij}$ is calculated using $A_{ij}=(p_i-p_j)/(p_i+p_j)$. If $p_i$ and $p_j$ are the same, the asymmetry value $A_{ij}$ is zero and a determination is made that the radiation beam is symmetric. If the asymmetry value $A_{ij}$ is not zero, a determination is made that the beam is not symmetric. In such a case, the asymmetry value represents the amount by which the radiation beam is offset from the collimator rotation axis. Optionally, in step S108, the tilt is determined based on the calculated asymmetry value, and in step S109, the angle of incidence of the electron pencil beam onto the target is adjusted based on the determined tilt.

In alternate embodiments, if the difference between $p_i$ and $p_j$ is not zero, but falls within an acceptable value range (i.e., tolerance range), it is determined that the beam is symmetric, and if the difference between $p_i$ and $p_j$ does not fall within an acceptable value range, it is determined that the beam is not symmetric.

Adjusting the angle of incidence of the electron pencil beam onto the X-ray target 118 can be accomplished by adjusting the angle steering coils in the radial and transverse directions, or with mechanical adjustments of the guide on low energy radiation treatment devices. Since the angle of incidence of the electron pencil beam onto the X-ray target 118 is adjusted by adjusting the angle steering coils in the radial and transverse directions, the angle steering coils of the radiation treatment device 103 are calibrated in the radial and transverse angles so that the electron pencil beam hits the X-ray target 118 at a perpendicular angle, or the guide is mechanically adjusted. If it is determined that the beam is not properly aligned, a signal is sent to the controller 120 to automatically adjust the angle steering coils in the radial and transverse directions.

Figure 18:
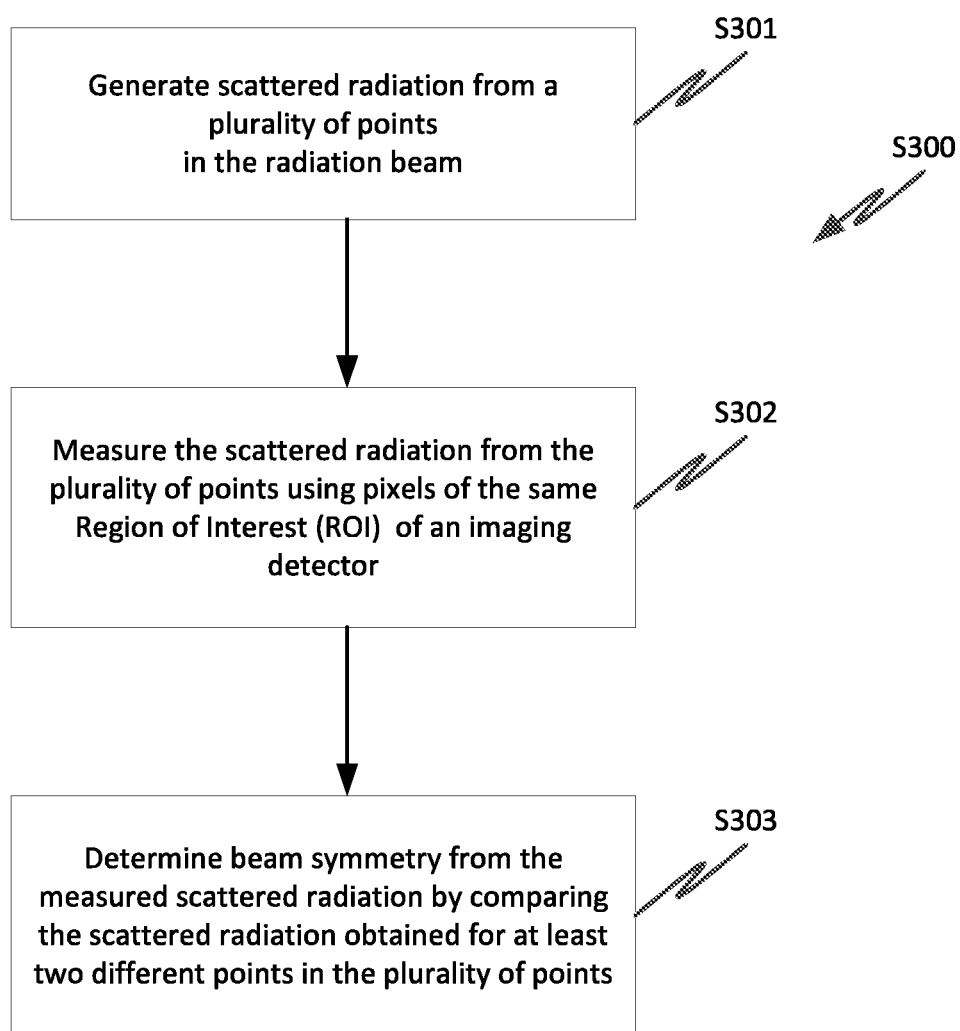
FIG. 18 illustrates an exemplary flow diagram for determining beam symmetry based on measured scattered radiation using an EPID according to an embodiment.

In another exemplary process S300 shown in FIG. 18, beam symmetry is determined by first generating scattered radiation from a plurality of locations in the radiation beam (S301), then measuring the scattered radiation from the plurality of locations using pixels of the same region of interest (ROI) of an imaging device (S302), followed by determining beam symmetry from the measured scattered radiation by comparing the scattered radiation obtained for at least two different locations in the plurality of locations (S303), the two locations being symmetric to each other relative to the radiation beam axis. If the scattered radiation is the same for two of the plurality of locations which are symmetric to each other relative to the radiation beam axis, or the difference between the measured scattered radiation falls within a previously determined acceptable range, the beam is determined to be symmetric. Otherwise, the beam is asymmetric and a beam asymmetry value is calculated based on the measured scattered radiations for the two locations. Optionally, a tilt of the radiation beam is determined based on the calculated asymmetry value. The system 100 can also be calibrated based on the determined tilt. The calibration can be automatic, manual, or a combination of the two.

System Calibration Using EPID

Figure 19:
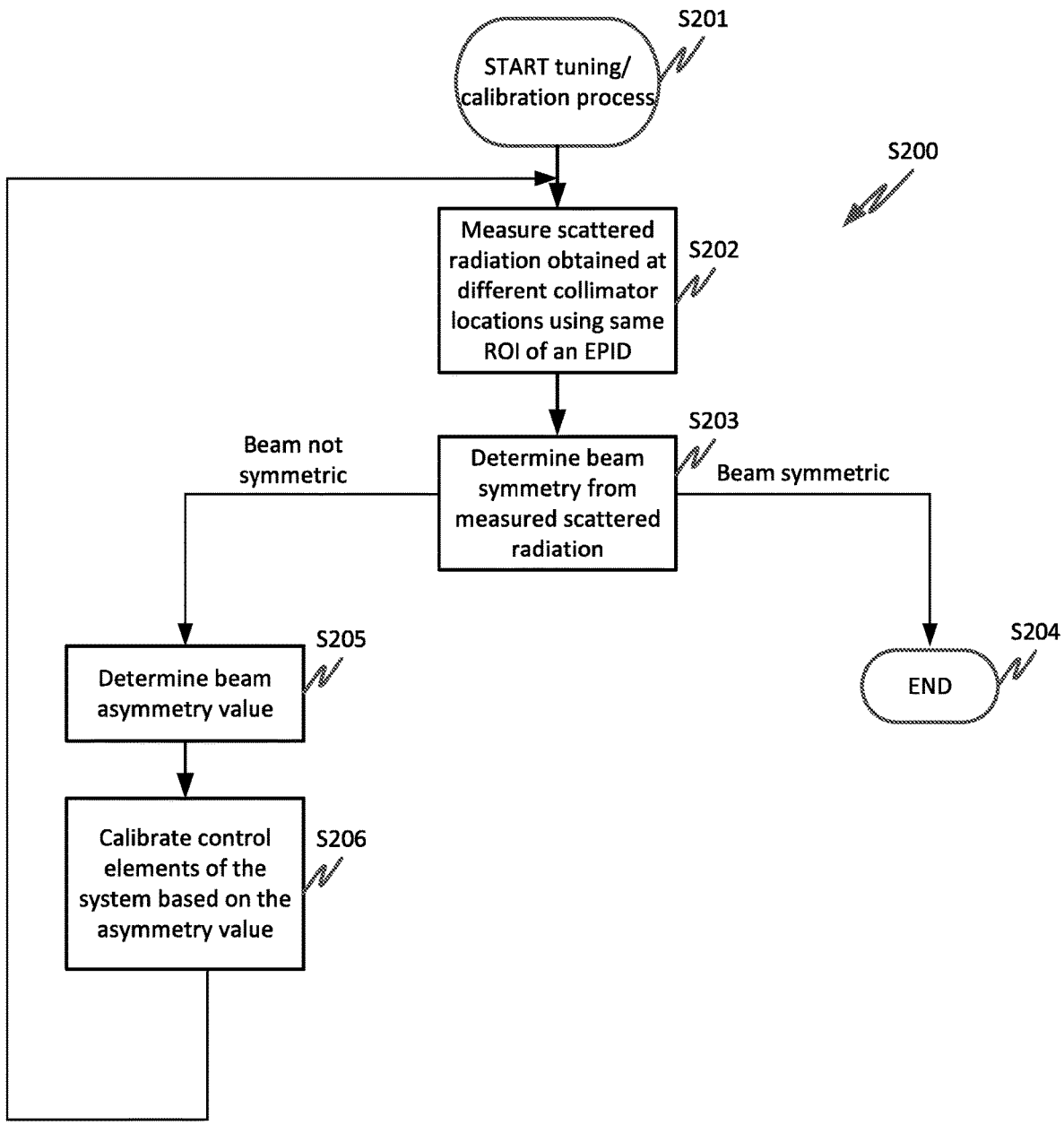
FIG. 19 illustrates an exemplary flow diagram for a calibration process using an EPID according to one or more embodiments of the disclosed subject matter.

An exemplary automatic tuning/calibration process S200 by which the system 100 is tuned/calibrated with an EPID to operate within expected parameters is shown in FIG. 19. The process S200 includes measuring, using an electronic portal imaging device (EPID), the scattered radiation obtained at different collimator locations using the same region of interest ROI of the EPID (S202), the radiation having been scattered by a scatter probe simulated by an off-axis field generated in the radiation treatment system 100, and determining beam symmetry from the measured scattered radiation in S203. If it is determined in S203 that the beam is not symmetric, a beam asymmetry value S205 is calculated based on the measured scattered radiation in S203, followed by the step of tuning/calibrating the control elements of the system 100 (S206) based on the calculated asymmetry value so as to ensure that the mechanical and geometric integrity of the radiation treatment device 103 is maintained. The process is repeated until it is determined in step S203 that the beam is symmetric. At such time, the process ends at S204. Process S200 includes steps which use the EPID 112 to measure a radiation beam asymmetry value and use of the beam asymmetry value for the mechanical element calibration/tuning/adjustment process by which the radiation beam is aligned.

The calibration process S200 includes a plurality of calibration tasks which could be fully or partially automatically performed using an electronic portal imaging device EPID 112. The starting of the tuning/calibration process S200 can be initiated at the controller 120 in Step S201, or via a second computer adapted to communicate with controller 120 to execute the calibration tests. In one embodiment, the process S200 provides for an automated test sequence that quickly determines beam asymmetry and completes tests to help medical physicists determine whether the radiation therapy system is operating within specified parameters prior to treatment.

Figure 20:
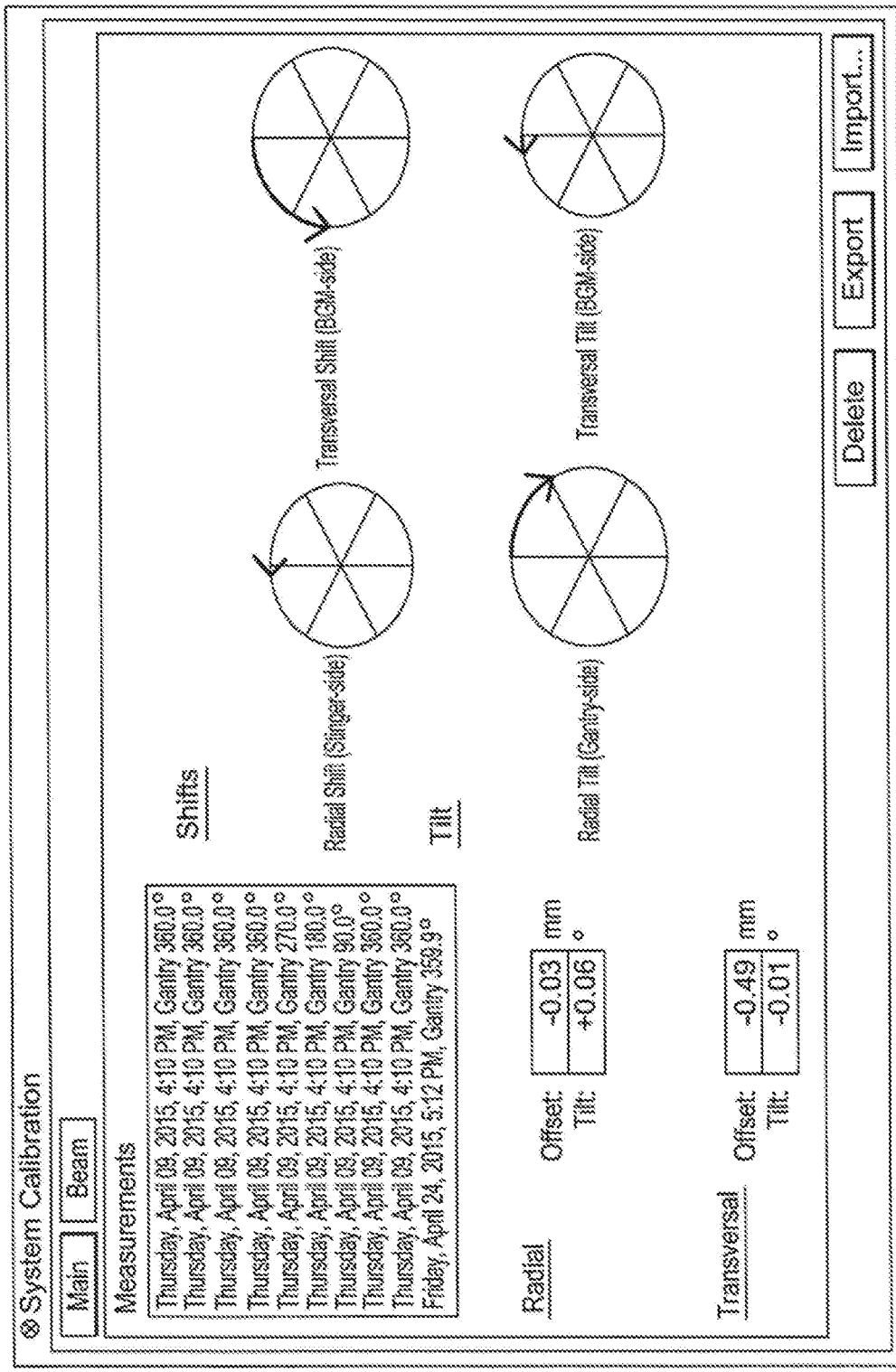
FIG. 20 illustrates an example for graphical indicators for bolt turns to correct misalignment according to an exemplary embodiment.

Using the EPID 112 in the process S200 allows for the determination of beam symmetry change with respect to a reference (e.g., baseline). The determined discrepancies between the measured beam symmetry values and the baseline beam symmetry values can be displayed for service purposes, as shown in FIG. 20, so that the angle steering coil could be adjusted accordingly.

The system calibration process S200 also includes determining beam tilt and initiating the appropriate calibration of the beam if a determination is made that there is a beam tilt relative to the collimator rotation axis. The process S200 provides the ability to measure radial and transversal source offset and tilt with gantry at any position. The calibration process S200 also provides the ability to review completed measurements at any time, as well as visual indicators for suggested alignment procedures including alignment bolts correction turns, as shown in FIG. 20.

Embodiments described herein therefore provide systems and methods where an EPID can be used as a measurement device for measuring different parameters of the radiation treatment system, without having to implement a complex calibration of the EPID. The general process by which the radiation treatment system and device 103 is automatically calibrated using an electronic portal imaging device (EPID) includes the steps of evaluating various parameters of the radiation treatment device 103, followed by the automatic tuning of various elements of the radiation treatment device in response to the result of the evaluation. This can be achieved by measuring scattered radiation from different locations of a scatter probe (off-axis field) in a radiation field using the same predetermined region of interest ROI of the EPID 112 and determining a parameter of the radiation treatment device 103. This parameter can be any one of beam symmetry, tilt, and beam alignment.

Then each parameter is evaluated to determine whether it falls within a prescribed range. If the parameter falls within a prescribed range, the process steps are repeated to determine and evaluate another parameter of the radiation treatment device 103. If the parameter does not fall within a prescribed range, the output of a control element of the radiation treatment device 103 affecting the respective parameter is adjusted until the parameter falls within the prescribed range. The adjustment can include an adjustment in the radiation limiting (collimating) devices, the angle and position of the steering coils, the location of the flattening filters 117, the size of the bend magnet shunt current, and the position and symmetry of the ionization chamber 119, for example. The adjustment can also be done manually, where appropriate. For example, manual adjustment of mechanical screws, bolts, or any other mechanical pieces of the radiation treatment system can be manually done.

This calibration process can be automatically repeated until some or all parameters of the device are evaluated and the corresponding control element outputs adjusted. Any number of automatic routines using any different type of feedback device can be inserted in the calibration process with the same iterative tuning. When all the outputs are tuned and the evaluated parameters fall within prescribed ranges, the radiation treatment device 103 is properly tuned, and the process stops.

It will be appreciated that the processes, systems, and sections described above can be implemented in hardware, hardware programmed by software, software instruction stored on a non-transitory computer readable medium or a combination of the above. For example, a method can be implemented using a processor configured to execute a sequence of programmed instructions stored on a non-transitory computer readable medium. The processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms.

Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, systems, methods, devices, and algorithms for using an EPID as a measuring device for beam tilt and beam asymmetry determination without having to calibrate the EPID. It is thus also apparent that there is provided in accordance with the present disclosure, systems, methods, devices, and algorithms for using an EPID as an imaging device for calibrating a radiation treatment system without needing to implement extensive and complex calibration procedures.

Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

What is claimed is:

1. A method for determining a radiation beam tilt relative to a collimator axis of rotation of a radiation treatment device, comprising:
   emitting a radiation beam from a source positioned at the collimator axis of rotation, the radiation beam passing through an aperture of the collimator positioned around the collimator axis at a first position so as to be received by an electronic portal imaging device positioned at a distance from the source along the collimator axis of rotation;
   measuring intensity of the radiation beam received by the electronic portal imaging device;
   rotating the collimator around the collimator axis by 180 degrees to a second position and measuring the intensity of the radiation beam that passes through the aperture by the electronic portal imaging device,
   comparing the intensity of the radiation beam measured at the first location of the collimator and the intensity of the radiation beam measured at the second location of the collimator,
   calculating an asymmetry value from the difference in the measured intensities; and
   calculating radiation beam tilt from the asymmetry value.

2. The method of claim 1, further comprising determining whether the beam tilt is a radial or a transversal tilt relative to the collimator axis of rotation.

3. The method of claim 2, further comprising initiating a calibrating process to adjust the determined radiation beam tilt.

4. The method of claim 3, wherein the calibrating process includes one a manual or automatic adjustment.

5. The method of claim 4, wherein the adjusting includes adjusting one or more of radiation collimating devices, angle and position of steering coils, location of flattening filters, size of a bend magnet shunt current, position and/or symmetry of an ionization chamber, and mechanical elements of the radiation system.

6. The method of claim 5, wherein the manual adjustment includes adjusting mechanical screws, bolts, or other mechanical pieces of the radiation treatment device.

7. The method of claim 6, wherein the adjusting is configured to be repeated until the tilt falls within a prescribed range.

8. The method of claim 7, further comprising displaying completed adjustments and suggested alignments to a user.

9. A non-transitory computer-readable medium including instructions to be executed by a computer processor to determine radiation beam tilt relative to a collimator rotation axis of a radiation treatment device, which when executed by the computer:
   sends a signal to a radiation source to emit a radiation beam from a source positioned at the collimator axis of rotation, the radiation beam passing through an aperture of the collimator positioned around the collimator axis at a first position so as to be received by an electronic portal imaging device positioned at a distance from the source along the collimator axis of rotation;
   initiates the measuring of intensity of the radiation beam received by the electronic portal imaging device;
   controls the rotating of the collimator around the collimator axis by 180 degrees to a second position and initiates measuring of the intensity of the radiation beam that passes through the aperture by the electronic portal imaging device;
   initiates comparing the intensity of the radiation beam measured at the first location of the collimator and the intensity of the radiation beam measured at the second location of the collimator;
   calculates an asymmetry value from the difference in the measured intensities; and
   calculates radiation beam tilt from the asymmetry value.

10. The non-transitory computer-readable medium of claim 9, further comprising determining whether the beam tilt is a radial or a transversal tilt relative to the collimator axis of rotation.

11. The non-transitory computer-readable medium of claim 10, further comprising initiating a calibrating process to adjust the determined radiation beam tilt.

12. The non-transitory computer-readable medium of claim 11, wherein the calibrating process includes one a manual or automatic adjustment, and wherein the adjusting includes adjusting one or more of radiation collimating devices, angle and position of steering coils, location of flattening filters, size of a bend magnet shunt current, position and/or symmetry of an ionization chamber, and mechanical elements of the radiation system.

* * * * *